US008362033B1

(12) United States Patent
Cuevas

(10) Patent No.: US 8,362,033 B1
(45) Date of Patent: Jan. 29, 2013

(54) COMPOUNDS AND METHODS TO DYSREGULATE $CA^{2+}$ HOMEOSTASIS FOR CANCER TREATMENT

(75) Inventor: Javier Cuevas, Lutz, FL (US)

(73) Assignee: University of South Florida, Tampa, FL (US)

(*) Notice: Subject to any disclaimer, the term of this patent is extended or adjusted under 35 U.S.C. 154(b) by 540 days.

(21) Appl. No.: 12/554,512

(22) Filed: Sep. 4, 2009

Related U.S. Application Data

(60) Provisional application No. 61/094,313, filed on Sep. 4, 2008.

(51) Int. Cl.
*A61K 31/47* (2006.01)
*A61K 31/69* (2006.01)

(52) U.S. Cl. .......................... 514/312; 514/64

(58) Field of Classification Search .................. None
See application file for complete search history.

(56) References Cited

U.S. PATENT DOCUMENTS

| 2002/0107193 | A1* | 8/2002 | Glazner | 514/12 |
| 2010/0311678 | A1* | 12/2010 | Bean et al. | 514/34 |

OTHER PUBLICATIONS

Krug et al., "New Molecular Therapy Targets in Acute Myeloid Leukemia," Recent Results in Cancer Res., 2007, Vo. 176, pp. 243-261.*
Sebti, et al., Farnesyltransferase Inhibitors, Seminars in Oncology, 2004, vol. 31, No. 1, Suppl. 1, pp. 28-39.
Pratt, et al., Immunodeficiency and Immunotherapy in Multiple Myeloma, British Journal of Haematology, 2007, vol. 138, pp. 563-579.
Peter, et al., Mechanisms of CD95 (APO-1/Fas)-Mediated Apoptosis, Current Opinion in Immunology, 1998, vol. 10, pp. 545-551.
Mayur, et al., Design of New Drug Molecules be Used in Reversing Multidrug Resistance in Cancer Cells, Current Cancer Drug Targets, 2009, vol. 9, pp. 298-306.
Tucci, et al., Role of Active Drug Transporters in Refractory Multiple Myeloma, Current Topics in Medicinal Chemistry, 2009, vol. 9, pp. 218-224.
Wu, et al., Characteristics of Store-Operated Ca2+-Permeable Current in Monocytic U937 Cells, Chinese Journal of Physiology, 1997, vol. 40, No. 3, pp. 115-120.
Lentzsch, et al., Pathophysiology of Multiple Myeloma Bone Disease, Hematology/Oncolgy Clinics of North America, 2007, vol. 21, pp. 1035-1049.
Putney, A Model for Receptor-Regulated Calcium Entry, Cell Calcium, 1986, vol. 7, pp. 1-12.
U.S. Government Statistics N (2009) Surveillance, Epidemiology, and End Results Program, U.S. Department of Health and Human Services, National Institutes of Health, National Cancer Institute.
Parekh, et al., Store-Operated Calcium Channels, Physiology Review, 2005, vol. 85, pp. 757-810.
Zhang, et al., TRPM2 is an Ion Channel that Modulates Hematopoietic Cell Death Through Activation of Caspases and PARP Cleavage, American Journal Physiology Cell Physiology, 2006, vol. 290, pp. C1146-C1159.
Yanamandra, et al., Tipifarnib and Bortezomib are Synergistic and Overcome Cell Adhesion-Mediated Drug Resistance in Multiple Myeloma and Acute Myeloid Leukemia, Clinical Cancer Research, 2006, vol. 12, No. 2, pp. 591-599.
Xu, et al., Block of TRPC5 Channels by 2-Aminoethoxydiphenyl Borate: A Differential, Extracellular and Voltage-Dependent Effect, British Journal of Pharmacology, 2005, vol. 145, pp. 405-414.
Willmott, et al., Functional Importance of the Dihydropyridine-Sensitive, yet Voltage-Insensitive Store-Operated Ca2+ Influx of U937 Cells, FEBS Letters, 1996, vol. 394, pp. 159-164.
Trudel, et al., The Inhibitory Anti-FGFR3 Antibody, PRO-001, is Cytotoxic to t(4;14) Multiple Myeloma Cells, Blood, 2006, vol. 107, No. 10, pp. 4039-4046.
Sun, et al., Antitumor Efficacy of a Novel Class of Non-Thiol-Containing Peptidomimetic Inhibitors of Farnesyltransferase and Geranylgernyltranferase I: Combination Therapy with the Cytotoxic Agents Cisplatin, Taxol, and Gemcitabine, Cancer Research, 1999, vol. 59, pp. 4919-4926.
Silvestris, et al., Negative Regulation of Erythroblast Maturation by Fas-L+/TRAIL+ Highly Malignant Plasma Cells: A major Pathogenetic Mechanism of Anemia in Multiple Myeloma, Blood, 2002, vol. 99, No. 4, pp. 1305-1313.
Pahl, et al., Activation of Transcription Factor NF-kB by the Adenovirus E3/19K Protein Requires its ER Retention, The Journal of Cell Biology, 1996, vol. 132, No. 4, pp. 511-522.
Santucci, et al., Farnesyltransferase Inhibitors and Their Role in the Treatment of Multiple Myeloma, Cancer Control, 2003, vol. 10, No. 5, pp. 384-387.
Li, et al., Tumor Microenvironment and Drug Resistance in Hematologic Malignancies, Blood Reviews, 2006, vol. 20, pp. 333-342.
Li, et al., Functional Characterization of Homo- and Heteromeric Channel Kinases TRPM6 and TRPM7, The Journal of General Physiology, 2006, vol. 127, No. 5, pp. 525-537.
Schindl, et al., 2-Aminoethoxydiphenyl Borate Alters Selectivity of Orai3 Channels by Increasing Their Pore Size, The Journal of Biological Chemistry, 2008, vol. 283, No. 29, pp. 20261-20267.
Dehaven, et al., VPAC Receptor Modulation of Neuroexcitability in Intracardiac Neurons, The Journal of Biological Chemistry, 2004, vol. 279, No. 39, pp. 40609-40621.
Gu, et al., Light-Chain-Mediated Acute Tubular Interstitial Nephritis, Arch. Pathol. Lab. Med., 2006, vol. 130, pp. 165-169.

(Continued)

*Primary Examiner* — Sreeni Padmanabhan
*Assistant Examiner* — Jody Karol
(74) *Attorney, Agent, or Firm* — Robert J. Varkonyi; Smith & Hopen, P.A.

(57) ABSTRACT

Disclosed is a novel composition and method for chemotherapy in leukemia. Activation of the calcium ion channel by tipifarnib increases intracellular calcium and triggers cell death in leukemia cell lines. Increasing the activity of this channel with 2-aminoethoxydiphenyl borate (2-APB) enhances both the intracellular calcium elevations and cell death, whereas decreasing the activity of the channel with gadolinium or lanthanum blocks the calcium increases and promotes cell survival. The protein target was able to overcome cell adhesion-mediated drug resistance, which often limits the usefulness of other targets. This protein is expressed in other immortalized cell lines, but has limited expression in normal native cell types in humans. Such limited expression would reduce the likelihood of adverse side effects associated with the targeting of this protein.

7 Claims, 14 Drawing Sheets

OTHER PUBLICATIONS

Gu, et al., 2-Aminoethoxydiphenyl Borate Stimulates Pulmonary C Neurons Via the Activation of TRPV Channels, Am. J. Physiol. Lung Cell Mol. Physiol., 2005, vol. 288, No. 5, pp. L932-L941.

Harousseau, et al.; "A Randomized Phase 3 Study of Tipifarnib Compared With Best Supportive Care, Including Hydroxyurea, in the Treatment of Newly Diagnosed Acute Myeloid Leukemia in Patients 70 Years or Older", Blood Journal, vol. 114, No. 6, pp. 1166-1173; 2009.

Lievremont, et al.; "Mechanism of Inhibition of TRPC Cation Channels by 2-Aminoethoxydiphenylborane"; Molecular Pharmacology; vol. 68, No. 3, pp. 758-762; 2005.

Raponi, et al., A 2-Gene Classifier for Predicting Response to the Farnesyltransferase Inhibitor Tipifarnib in Acute Myeloid Leukemia, Blood, 2008, vol. 111, No. 5, pp. 2589-2596.

Rao, et al., Coupling Endoplasmic Reticulum Stress to the Cell Death Program, Cell Death and Differentiation, 2004, vol. 11, pp. 372-380.

Raponi, et al., Identification of Molecular Predictors of Response in a Study of Tipifarnib Treatment in Relapsed and Refractory Acute Myelogenous Leukemia, Clinical Cancer Research, 2007, vol. 13, No. 7, pp. 2254-2260.

Reece, Management of Multiple Myeloma: The Changing Landscape, Blood Reviews, 2007, vol. 21, pp. 301-314.

Dalton, et al., Multiple Myeloma, Hematology, 2001, pp. 157-177.

Bird, et al., Methods for Studying Store-Operated Calcium Entry, Methods, 2008, vol. 46, pp. 204-212.

Zhu, et al., Farnesyltransferase Inhibitor R115777 (Zarnestra, Tipifarnib) Synergizes with Paclitaxel to Induce Apoptosis and Mitotic Arrest and to Inhibit Tumor Growth of Multiple Myeloma Cells, Blood, 2005, vol. 105, No. 12, pp. 4759-4766.

Brandman, et al., STIM2 is a Feedback Regulator that Stabilizes Basal Cytosolic and Endoplasmic Reticulum Ca2+ Levels, Cell, 2007, vol. 131, pp. 1327-1339.

Beaupre, et al., Farnesyl Transferase Inhibitors Enhance Death Receptor Signals and Induce Apoptosis in Multiple Myeloma Cells, Leukemia & Lymphoma, 2003, vol. 44, No. 12, pp. 2123-2134.

Beaupre, et al., R115777 Induces Ras-Independent Apoptosis of Myeloma Cells Via Multiple Intrinsic Pathways, Molecular Cancer Therapeutics, 2004, vol. 2, pp. 179-186.

Asoh, et al., Synthesis and Structure-Activity Relationships of Novel Benzofuran Farnesyltransferase Inhibitors, Bioorganic & Medicinal Chemistry Letters, 2009, vol. 19, pp. 1753-1757.

Ashar, et al., Farnesyl Transferase Inhibitors Block the Farnesylation of CENP-E and CENP-F and Alter the Association of CENP-E with the Microtubules, The Journal of Biological Chemistry, 2000, vol. 275, No. 39, pp. 30451-30457.

Alsina, et al., Farnesyltransferase Inhibitor Tipifarnib is Well Tolerated, Induces Stabilization of Disease, and Inhibits Farnesylation and Ocogenic/Tumor Survival Pathways in Patients with Advanced Multiple Myeloma, Blood, 2004, vol. 103, No. 9, pp. 3271-3277.

Alnemri, Mammalian Cell Death Proteases: A Family of Highly Conserved Aspartate Specific Cysteine Proteases, Journal of Cellular Biochemistry, 1997, vol. 64, pp. 33-42.

DeHaven, et al., Calcium Inhibition and Calcium Potentiation of Orai1, Orai2, and Orai3 Calcium Release-Activated Calcium Channels, The Journal of Biological Chemistry, 2007, vol. 282, No. 24, pp. 17548-17556.

DeHaven, et al., Complex Actions of 2-Aminoethyldiphenyl Borate on Store-Operated Calcium Entry, The Journal of Biological Chemistry, 2008, vol. 283, No. 28, pp. 19265-19273.

Damiano, et al., Cell Adhesion Medicated Drug Resistance (CAM-DR): Role of Integrins and Resistance to Apoptosis in Human Myeloma Cell Lines, Blood, 1999, vol. 93, No. 5, pp. 1658-1667.

Cuevas, et al., Mammalian Nicotinic Receptors with Alpha7 Subunits That Slowly Desensitize and Rapidly Recover from Alpha-Bungarotoxin Blockade, The Journal of Neuroscience, 1998, vol. 18, No. 24, pp. 10335-10344.

Chiu, et al., Soft Substrate Up-Regulates the Interaction of STIM1 with Store-Operated Ca2+ Channels that Lead to Normal Epithelial Cell Apoptosis, Molecular Biology of the Cell, 2008, vol. 19, pp. 2220-2230.

Chinnaiyan, The Apoptosome: Heart and Soul of the Cell Death Machine, Neoplasia, 1999, vol. 1, No. 1, pp. 5-15.

Buzzeo, et al., Characterization of a R115777-Resistant Human Multiple Myeloma Cell Line with Cross-Resistance to PS-341, Clinical Cancer Research, 2005, vol. 11, No. 16, pp. 6057-6064.

Hazlehurst, et al., Reduction in Drug-Induced DNA Double-Strand Breaks Associated with Beta 1 Integrin-Mediated Adhesion Correlates with Drug Resistance in U937 Cells, Blood, 2001, vol. 98, No. 6, pp. 1897-1903.

Hazlehurst, et al., Adhesion to Fibronectin via Beta 1 Integrins Regulates p27kip1 Levels and Contributes to Cell Adhesion Mediated Drug Resistance (CAM-DR), Oncogene, 2000, vol. 19, pp. 4319-4327.

Hazlehurst, et al., Mechanisms Associated with Cell Adhesion Mediated Drug Resistance (CAM-DR) in Hematopoietic Malignancies, Cancer and Metastasis Reviews, 2001, vol. 20 pp. 43-50.

Gross, et al., Murine ORAI2 Splice Variants Form Functional Ca2+ Release-Activated Ca2+ (CRAC) Channels, The Journal of Biological Chemistry, 2007, vol. 282, No. 27, pp. 19375-19384.

Ferri, et al., Organelle-Specific Initiation of Cell Death Pathways, Nature Cell Biology, 2001, vol. 3, pp. E255-E263.

Fadeel, et al., Apoptosis in Human Disease: A New Skin for the Old Ceremony?, Biochemical and Biophysical Research Communications, 1999, vol. 266, pp. 699-717.

Facon, et al., Dexamethasone-Based Regimens Versus Melphalan-Prednisone for Elderly Multiple Myeloma Patients Ineligible for High-Dose Therapy, Blood, 2006, vol. 107, No. 4, pp. 1292-1298.

Kurzrock, et al., Farnesyltransferase Inhibitor R 115777 in Myelodysplastic Syndrome: Clinical and Biologic Activities in the Phase 1 Setting, Blood, 2003, vol. 102, No. 13, pp. 4527-4534.

Kraft, et al., Hydrogen Peroxide and ADP-Ribose Induce TRPM2-Mediated Calcium Influx and Cation Currents in Microglia, American Journal Physiology Cell Physiology, 2003, vol. 286, pp. C129-C137.

Kohl, Farnesyltransferase Inhibitors Preclinical Development, Anals New York Academy of Sciences, pp. 91-102, Dec. 1999.

Karp, et al., Clinical and Biologic Activity of the Farnesyltransferase Inhibitor R115777 in Adults with Refractory and Relapsed Acute Leukemias: A Phase 1 Clinical-Laboratory Correlative Trial, Blood, 2001, vol. 97, No. 11, pp. 3361-3369.

Johnston, et al., Farnesyl Transferase Inhibitors—A Novel Therapy for Breast Cancer, Endocrine-Related Cancer, 2001, vol. 8, pp. 227-235.

Jiang, et al., The Phosphoinositide 3-OH Kinase/AKT2 Pathway as a Critical Target for Farnesyltransferase Inhibitor-Induced Apoptosis, Molecular and Cellular Biology, 2000, vol. 20, No. 1, pp. 139-148.

Hitomi, et al., Involvement of Caspase-4 in Endoplasmic Reticulum Stress-Induced Apoptosis and ABeta-Induced Cell Death, The Journal of Cell Biology, 2004, vol. 165, No. 3, pp. 347-356.

Hazlehurst, et al., Role of the Tumor Microenvironment in Mediating De Novo Resistance to Drugs and Physiological Mediators of Cell Death, Oncogene, 2003, vol. 22, pp. 7396-7402.

Lerner, et al., Ras CAAX Peptidomimetic FTI-277 Selectivity Blocks Oncogenic Ras Signaling by Inducing Cytoplasmic Accumulation of Inactive Ras-Raf Complexes, The Journal of Biological Chemistry, 1995, vol. 270, No. 45, pp. 26802-26806.

Lee, et al., Characterization of Ca2+ Influx Induced by Dimethylphytosphingosine and Lysophosphatidylcholine in U937 Monocytes, Biochemical and Biophysical Research Communications, 2006, vol. 348, pp. 1116-1122.

Lee, et al., IRE1-Mediated Unconventional mRNA Splicing and S2P-Mediated ATF6 Cleavage Merge to Regulate XBP1 in Signaling the Unfolded Protein Response, Genes & Development, 2002, vol. 16, pp. 452-466.

Landowski, et al., Mitochondrial-Mediated Disregulation of Ca2+ is a Critical Determinant of Velcade (PS-341/Bortezomib) Cytotoxicity in Myeloma Cell Lines, Cancer Research, 2005, vol. 65, No. 9, pp. 3828-3936.

Lai, et al., Endoplasmic Reticulum Stress: Signaling the Unfolded Protein Response, Physiology, 2007, vol. 22, pp. 193-201.

Monteilh-Zoller, et al., TRPM7 Provides an Ion Channel Mechanism for Cellular Entry of Trace Metal Ions, The Journal of General Physiology, 2003, vol. 121, pp. 49-60.

Matsunaga, et al., Interaction Between Leukemic-Cell VLA-4 and Stromal Fibronectin is a Decisive Factor for Minimal Residual Disease of Acute Myelogenous Leukemia, Nature Medicine, 2003, vol. 9, No. 9, pp. 1158-1165.

Mitsiades, et al., The Proteasome Inhibitor PS-341 Potentiates Sensitivity of Multiple Myeloma Cells to Conventional Chemotherapeutic Agents: Therapeutic Applications, Blood, 2003, vol. 101, No. 6, pp. 2377-2380.

Ludwig, et al., Thalidomide-Dexamethasone Compared with Melphalan-Prednisolone in Elderly Patients with Multiple Myeloma, Blood, 2009, vol. 113, No. 15, pp. 3435-3442.

Orrenius, et al., Regulation of Cell Death: The Calcium-Apoptosis Link, Nature Reviews, 2003, vol. 4, pp. 552-565.

Nefedova, et al., Bone Marrow Stromal-Derived Soluble Factors and Direct Cell Contact Contribute to De Novo Drug Resistance of Myeloma Cells by Distinct Mechanisms, Leukemia, 2003, vol. 17, pp. 1175-1182.

Nakagawa, et al., Caspase-12 Mediates Endoplasmic-Reticulum-Specific Apoptosis and Cytotoxicty by Amyloid-Beta, Nature, 2000, vol. 403, pp. 98-103.

Nadler, et al., LTRPC7 is a Mg.ATP-Regulated Divalent Cation Channel Required for Cell Viability, Nature, 2001, vol. 411, pp. 590-595.

Qing, et al., Antibody-Based Targeting of FGFR3 in Bladder Carcinoma and t(4;14)-Positive Multiple Myeloma in Mice, The Journal of Clinical Investigation, 2009, vol. 119, No. 5, pp. 1216-1229.

* cited by examiner

COMPOUNDS AND METHODS TO DYSREGULATE CA$^{2+}$ HOMEOSTASIS FOR CANCER TREATMENT

CROSS REFERENCE TO RELATED APPLICATION

This application claims priority to currently pending U.S. Provisional Patent Application No. 61/094,313, entitled "Dysregulation of Ca$^{2+}$ Homeostasis by Tipifarnib Induces Apoptosis in Acute Myeloid Leukemia Cells", filed on Sep. 4, 2008, the contents of which are herein incorporated by reference.

GOVERNMENT SUPPORT STATEMENT

This invention was made with government support under grant number 5K12 CA 87989-02 awarded by the National Institutes of Health. The government has certain rights in the invention.

FIELD OF INVENTION

This invention relates to the field of cancer therapy.

BACKGROUND OF THE INVENTION

A major contributing factor to the high mortality rate associated with acute myeloid leukemia (AML) is the development of resistance to chemotherapy and death receptor-mediated apoptosis. Multiple myeloma (MM) is one of the most common hematological malignancies, involving bone marrow plasmacytosis. Multiple myeloma (MM) is currently incurable, with approximately 20,000 newly diagnosed cases per year and the current median survival is 3-5 years. Uncontrolled proliferation of plasma cells in the bone marrow ultimately leads to hematopoietic failure and skeletal destruction. Oncogene mutations, translocations in immunoglobulin enhancers, and cytogenetic changes result in progression from a germinal center B cell to multiple myeloma, which occurs in approximately 1%-3% of the adult population (Dalton W S, et al. (2001) Multiple myeloma. *Hematology Am Soc Hematol Educ Program*: 157-177).

Invasion of the bone marrow by the malignant plasma cell neoplasm leads to hematopoietic failure, clotting via thrombocytopenia, anemia via diminished erythrocyte production and survival (Silvestris F, et al. (2002) Upregulation of erythroblast apoptosis by malignant plasma cells: a new pathogenetic mechanism of anemia in multiple myeloma. *Rev Clin Exp Hematol Suppl* 1:39-46; Silvestris F, et al. (2002) Negative regulation of erythroblast maturation by Fas-L(+)/TRAIL(+) highly malignant plasma cells: a major pathogenetic mechanism of anemia in multiple myeloma. *Blood* 99:1305-1313; Pratt G, et al. (2007) Immunodeficiency and immunotherapy in multiple myeloma. *Br J Haematol* 138: 563-579), and destruction of the skeleton through enhanced osteoclast activity and suppressing osteoblast differentiation (Lentzsch S, et al. (2007) Pathophysiology of multiple myeloma bone disease. *Hematol Oncol Clin North Am* 21:1035-1049, viii). Other complications of the disease, such as renal failure (Gu X and Herrera G A (2006) Light-chain-mediated acute tubular interstitial nephritis: a poorly recognized pattern of renal disease in patients with plasma cell dyscrasia. *Arch Pathol Lab Med* 130:165-169), also contribute to morbidity and mortality in the patients. MM is associated with a poor prognosis relative to lymphomas and leukemias in general, with a median life expectancy of 3-4 years (U.S. Government Statistics N (2009) Surveillance Epidemiology and End Results, in (Institute NC ed)).

There are currently various treatment options for the management of MM, influenced by various factors including patient age and eligibility for autologous stem cell transplantation (ASCT). Treatments include high-dose dexamethasone-based regimens, melphalan (Facon T, et al. (2006) Dexamethasone-based regimens versus melphalan-prednisone for elderly multiple myeloma patients ineligible for high-dose therapy. *Blood* 107:1292-1298), combinations of vincristine, doxorubicin (Adriamycin) and dexamethasone (Decadron) (Reece DE (2007) Management of multiple myeloma: the changing landscape. *Blood Rev* 21:301-314), thalidomide-like drugs (i.e. thalidomide and lenalidomide) and proteosome inhibitors (i.e. bortezomib). While some of these regimens have produced higher initial response rates, this has not translated into improved overall survival outcomes (Ludwig H, et al. (2009) Thalidomide-dexamethasone compared with melphalan-prednisolone in elderly patients with multiple myeloma. *Blood* 113:3435-3442). Thus, there is a significant need to develop novel therapeutic options that improve outcomes and extend survival. Surprisingly, the rate of relapse is consistent for both the various treatment regimens and initial response to treatment.

Cancer cells frequently evade chemotherapy-induced cell death via a process referred to as de novo drug resistance, which is likely one of the first steps involved in acquired drug resistance (Nefedova Y, et al. (2003) Bone marrow stromal-derived soluble factors and direct cell contact contribute to de novo drug resistance of myeloma cells by distinct mechanisms. *Leukemia* 17:1175-1182). The tumor microenvironment consists of stromal cells, extracellular matrix (ECM), and soluble factors including cytokines and growth factors. All of these components interact with tumor cells to contribute to de novo drug resistance (Li Z W and Dalton W S (2006) Tumor microenvironment and drug resistance in hematologic malignancies. *Blood Rev* 20:333-342), and the persistence of minimal residual disease with currently available drug regiments. This minimal residual disease ultimately permits relapse, regardless of the initial observable response. Of particular interest in this process is the ECM protein, fibronectin, (Hazlehurst L A and Dalton W S (2001) Mechanisms associated with cell adhesion mediated drug resistance (CAM-DR) in hematopoietic malignancies. *Cancer Metastasis Rev* 20:43-50; Hazlehurst L A, et al. (2000) Adhesion to fibronectin via beta1 integrins regulates p27kip1 levels and contributes to cell adhesion mediated drug resistance (CAM-DR). *Oncogene* 19:4319-4327). The adhesion of tumor cells to fibronectin cells and bone marrow stromal cells has been implicated in the cellular rearrangement of molecules involved in drug resistance. This particular form of de novo drug resistance is called cell adhesion-mediated drug resistance (CAM-DR), and the β1 integrin subunit appears to be a key player in development of this resistance.

Farnesyltransferase inhibitors are a novel class of anticancer agents developed to inhibit the enzyme farnesyltransferase that is responsible for the transfer of a farnesyl group to the Ras protein. FTIs were originally designed to inhibit Ras oncogenic activity, but recent studies suggest that FTIs may have several other targets including centromeric proteins and the phosphatidylinositide-3 kinase/Akt pathway (Ashar H R, et al. Farnesyl transferase inhibitors block the farnesylation of CENP-E and CENP-F and alter the association of CENP-E with the microtubules. J Biol. Chem. 2000 Sep. 29; 275(39): 30451-7; Jiang K, et al. The phosphoinositide 3-OH kinase/AKT2 pathway as a critical target for farnesyltransferase inhibitor-induced apoptosis. Mol Cell Biol. 2000 January;

20(1):139-48). To date, several FTIs have been clinically evaluated, including BMS-214664, SCH-66363 and R115777 for myelodysplastic syndrome, chronic myelogenous leukemia and acute leukemias (Johnston S R, Kelland L R. Farnesyl transferase inhibitors—a novel therapy for breast cancer. Endocr Relat Cancer. 2001 September; 8(3): 227-35; Karp J E, et al. Clinical and biologic activity of the farnesyltransferase inhibitor R115777 in adults with refractory and relapsed acute leukemias: a phase 1 clinical-laboratory correlative trial. Blood. 2001 Jun. 1; 97(11):3361-9; Kurzrock R, et al. Farnesyltransferase inhibitor R115777 in myelodysplastic syndrome: clinical and biologic activities in the phase 1 setting. Blood. 2003 Dec. 15; 102(13):4527-34). Tipifarnib (R115777) is a potent non-peptidomimetic inhibitor of farnesyltransferase (Kohl N E. Farnesyltransferase inhibitors. Preclinical development. Ann N Y Acad. Sci. 1999; 886:91-102; Santucci R, et al. Farnesyltransferase inhibitors and their role in the treatment of multiple myeloma. Cancer Control. 2003 September-October; 10(5):384-7; Sebti S M, Adjei A A. Farnesyltransferase inhibitors. Semin Oncol. 2004 February; 31(1 Suppl 1):28-39). Studies have demonstrated the anticancer activity of tipifarnib as a single agent or in combination in preclinical models for multiple myeloma and acute myeloid leukemia (Beaupre D M, et al. Farnesyl transferase inhibitors enhance death receptor signals and induce apoptosis in multiple myeloma cells. Leuk Lymphoma. 2003 December; 44(12):2123-34; Alsina M, et al. Farnesyltransferase inhibitor tipifarnib is well tolerated, induces stabilization of disease, and inhibits farnesylation and oncogenic/tumor survival pathways in patients with advanced multiple myeloma. Blood. 2004 May 1; 103(9): 3271-7; Yanamandra N, et al. Tipifarnib and bortezomib are synergistic and overcome cell adhesion-mediated drug resistance in multiple myeloma and acute myeloid leukemia. Clin Cancer Res. 2006 Jan. 15; 12(2):591-9; Zhu K, et al. Farnesyltransferase inhibitor R115777 (Zarnestra, Tipifarnib) synergizes with paclitaxel to induce apoptosis and mitotic arrest and to inhibit tumor growth of multiple myeloma cells. Blood. 2005 Jun. 15; 105(12):4759-66; Beaupre D M, et al. R115777 induces Ras-independent apoptosis of myeloma cells via multiple intrinsic pathways. Mol Cancer Ther. 2004 February; 3(2):179-86). However, the molecular mechanisms by which tipifarnib triggers cell death still remain elusive, and has not been unequivocally associated with farnesyltransferase inhibition.

Programmed cell death, or apoptosis, is a genetically controlled and evolutionary conserved mechanism required for normal development and tissue homeostasis (Fadeel B, et al. Apoptosis in human disease: a new skin for the old ceremony? Biochem Biophys Res Commun. 1999 Dec. 29; 266 (3):699-717). There are two main apoptotic pathways that trigger apoptosis and these are the extrinsic and intrinsic death pathways, respectively. The extrinsic pathway is triggered by the ligation of cell surface death receptors to death receptor ligands followed by formation of the death inducible signaling complex, which results in the activation of caspase-8 and subsequent downstream effectors (Peter M E, Krammer P H. Mechanisms of CD95 (APO-1/Fas)-mediated apoptosis. Curr Opin Immunol. 1998 October; 10(5):545-51; Alnemri E S. Mammalian cell death proteases: a family of highly conserved aspartate specific cysteine proteases. J Cell Biochem. 1997 January; 64(1):33-42). The intrinsic cell death pathway is initiated by mitochondrial release of cytochrome C, resulting in formation of the apoptosome complex and activation of caspase-9 (Chinnaiyan A M. The apoptosome: heart and soul of the cell death machine. Neoplasia. 1999 April; 1(1):5-15). Recently, a third pathway has been identified that is initiated by the endoplasmic reticulum (ER), and is known as the ER-stress pathway (Lai E, et al. Endoplasmic reticulum stress: signaling the unfolded protein response. Physiology (Bethesda). 2007 June; 22:193-201).

Studies have shown that pathways involved in cell death and $Ca^{2+}$ processing cross-talk, whereby activation of apoptotic cascades can interfere with the sequestration of $Ca^{2+}$ into intracellular pools. Conversely, disruption in $Ca^{2+}$ sequestration is sufficient to trigger apoptosis as a response to cellular stress (Orrenius S, et al. Regulation of cell death: the calcium-apoptosis link Nat Rev Mol Cell Biol. 2003 July; 4(7):552-65). Calcium storage and folding and sorting of newly synthesized proteins are the primary function of the mammalian ER. Imbalance in any of these processes can lead to ER stress, which in turn can activate at least two pathways. First, the unfolded protein response leads to induction of ER chaperons, such as GRP78, GRP94 and the transcription factor CHOP/GADD153 (Lai E, et al. Endoplasmic reticulum stress: signaling the unfolded protein response. Physiology (Bethesda). 2007 June; 22:193-201). Second, the ER overload response leads to activation of several signaling pathways including nuclear factor-κ-B (NF-κ-B) (Pahl H L, et al. Activation of transcription factor NF-kappaB by the adenovirus E3/19K protein requires its ER retention. J. Cell Biol. 1996 February; 132(4):511-22). Both responses help regulate the accumulation of misfolded proteins and enhance survival, but under severe stress they can also activate programmed cell death (Lee K, et al. IRE1-mediated unconventional mRNA splicing and S2P-mediated ATF6 cleavage merge to regulate XBP1 in signaling the unfolded protein response. Genes Dev. 2002 Feb. 15; 16(4):452-66).

Two basic components comprise environment-mediated drug resistance: physical contact between tumor cells and microenvironment components (cell adhesion mediated drug resistance, CAM-DR) and the local production of soluble factors. More specifically, in multiple myeloma and AML, it has been found that the adhesion of tumor cells (via integrin receptors) to fibronectin results in a drug-resistant phenotype (Hazlehurst L A, et al. Role of the tumor microenvironment in mediating de novo resistance to drugs and physiological mediators of cell death. Oncogene 2003; 22:7396-402; Matsunaga T, et al. Interaction between leukemic-cellVLA-4 and stromal fibronectin is a decisive factor for minimal residual disease of acute myelogenous leukemia. Nat Med 2003; 9:1158-65). Of importance, in a small series of AML patients, it was noted that those whose leukemic cells expressed VLA-4 (a4h1 integrin) had a high rate of relapse compared with those with low VLA-4 expression (Matsunaga T, et al. Interaction between leukemic-cellVLA-4 and stromal fibronectin is a decisive factor for minimal residual disease of acute myelogenous leukemia. Nat Med 2003; 9:1158-65). These results imply that the physical interaction between tumor cells and bone marrow constituents provides a refuge for minimal residual disease.

Many chemotherapeutic agents prompt apoptosis via the activation of one of these pathways. Cancer cells, however, frequently evade chemotherapy induced cell death via a process referred to as de novo drug resistance, which is likely one of the first steps involved in acquired drug resistance (Nefedova Y, et al. Bone marrow stromal-derived soluble factors and direct cell contact contribute to de novo drug resistance of myeloma cells by distinct mechanisms. Leukemia. 2003 June; 17(6):1175-82). A major contributing factor to the high mortality rate associated with acute myeloid leukemia (AML) and multiple myeloma (MM) is the development of resistance to chemotherapy and death receptor-mediated apoptosis. The tumor microenvironment consists of stromal cells, extracellular matrix (ECM), and soluble factors including cytokines and growth factors. All of these components interact with tumor cells to contribute to de novo drug resistance (Li Z W, Dalton W S. Tumor microenvironment and drug resistance in hematologic malignancies. Blood Rev. 2006 November; 20(6):333-42). Of particular interest in this process is the ECM protein, fibronectin (Hazlehurst L A, et al. Reduction in drug-induced DNA double-strand breaks associated with beta1 integrin-mediated adhesion correlates with drug resistance in U937 cells. Blood. 2001 Sep. 15; 98(6): 1897-903). Fibronectin is the ligand for at least ten integrin molecules that mediates cell adhesion (Li Z W, Dalton W S. Tumor microenvironment and drug resistance in hematologic malignancies. Blood Rev. 2006 November; 20(6):333-42). The adhesion of tumor cells to fibronectin and bone marrow stromal cells has been implicated in the cellular rearrangement of molecules involved in drug resistance including c-FLIP, Topoisomerase IIB, Fas and Bcl-2 (Hazlehurst L A, et al. Reduction in drug-induced DNA double-strand breaks associated with beta1 integrin-mediated adhesion correlates with drug resistance in U937 cells. Blood. 2001 Sep. 15; 98(6):1897-903). This particular form of de novo drug resistance is called cell adhesion-mediated drug resistance (CAM-DR). For example, in 15% of MM patient there is a t(4; 14) chromosomal translocation that results in overexpression of the tyrosine kinase receptor, fibroblast growth factor receptor 3 (FGFR3). Several studies have now shown that anti-FGFR3 antibodies are cytotoxic in t(4; 14)-positive multiple myeloma in mice and primary human t(4; 14)-positive MM cells (Trudel S, et al. (2006) The inhibitory anti-FGFR3 antibody, PRO-001, is cytotoxic to t(4; 14) multiple myeloma cells. *Blood* 107:4039-4046; Qing J, et al. (2009) Antibody-based targeting of FGFR3 in bladder carcinoma and t(4; 14)-positive multiple myeloma in mice. *J Clin Invest* 119: 1216-1229).

Multiple myeloma is an incurable hematologic malignancy that is the second most prevalent blood cancer after non-Hodgkin's lymphoma, affecting >56,000 people in the United States. While several new drugs have been identified in the last decade, and these treatments have increased the initial response rate; these new agents have failed to increase life expectancy. Moreover, these drugs have significant adverse effects that limit their usefulness. Thus, there is a great need for the identification of novel biomarkers and targets that will provide superior therapy for MM. Successful execution of the current proposal may reveal that Orai3 is such a biomarker/target, and provide a viable treatment alternative for a number of patients suffering from multiple myeloma. Tipifarnib would provide various treatment advantages over current drug regimens, including decreased toxicity, and may be quickly moved to clinical studies because of the substantial amount of human data already available for the drug.

Numerous proteins are involved in the movement of $Ca^{2+}$ including ATPases, transporters and channels; and various intracellular compartments including mitochondria and the endoplasmic reticulum (ER) serve as buffers and stores for $Ca^{2}±$. Dysregulation of intracellular $Ca^{2}±$, which triggers protein misfolding in the ER, is linked to numerous responses including lipolysis, proteolysis, and oxidative stress. The accumulation of unfolded/misfolded proteins in the ER lumen results in ER stress and activates the unfolded protein response (UPR) and the ER-associated degradation (ERAD). However, if the UPR is unable to resolve the underlying condition and ER stress becomes severe, programmed cell death is activated. Due to the ability of $Ca^{2+}$ to lead cells in this pathway, there is a considerable amount of interest in targeting intracellular $Ca^{2+}$ homeostasis for anticancer therapies.

Thus, there is a significant need to develop novel therapeutic options that improve outcomes and extend survival.

SUMMARY OF THE INVENTION

Studies have shown that the combination of tipifarnib, a non-peptidomimetic inhibitor of farnesyltransferase, with bortezomib, a proteosome inhibitor, promotes synergistic death, overcomes de novo drug resistance in AML cell lines, and stimulates the ER stress response synergistically in myeloma cells and overcomes CAM-DR (Yanamandra N, et al., Tipifarnib and bortezomib are synergistic and overcome cell adhesion-mediated drug resistance in multiple myeloma and acute myeloid leukemia. Clin Cancer Res 2006; 6:12, 591-599). Bortezomib alone dysregulates $[Ca^{2+}]_i$ and elicits ER stress in myeloma cells by inducing $Ca^{2+}$ from the mitochondria via a mechanism that appears to depend on the reversal of the mitochondrial $Ca^{2+}$ uniporter (Landowski T H, et al. Mitochondrial-mediated disregulation of $Ca^{2+}$ is a critical determinant of Velcade (PS-341/bortezomib) cytotoxicity in myeloma cell lines. Cancer Res. 2005 May 1; 65(9):3828-36). However, it remains to be determined if tipifarnib acts via an identical mechanism to induce cell death, or if the FTI is targeting a second molecular mechanism which also culminates in the induction of ER stress and concomitant cell death. Data presented here suggest that tipifarnib induces ER stress by acting at a distinct site from bortezomib, and that the effects of tipifarnib are not shared with other FTIs.

The molecular mechanisms by which tipifarnib produces cell death in the AML and MM cell lines, U937 and 8226, respectively, were analyzed. Tipifarnib treatment promotes elevations in intracellular free-calcium concentrations ($[Ca^{2+}]_i$) in U937 and 8226 cells. These increases in calcium are specific to tipifarnib and are not induced by other farnesyltransferase inhibitors (FTIs) tested (FTI-277 and FTI-2153). Experiments with specific inhibitors of ER and mitochondrial $Ca^{2+}$ release suggest that the elevations in $[Ca^{2+}]_i$ occur independent of $Ca^{2+}$ release from intracellular stores. Removal of extracellular $Ca^{2+}$ abolished the tipifarnib-induced increases in $[Ca^{2+}]_i$ indicating that they are due to plasmalemmal $Ca^{2+}$ influx. The elevations in $[Ca^{2+}]_i$ were also depressed by application of the $Ca^{2+}$ channel blockers, $Gd^{3+}$ or $La^{3+}$, but potentiated by 2-aminoethoxydiphenyl borate (2-APB). Blockade of $Ca^{2+}$ channels by $La^{3+}$ or $Gd^{3+}$ prevented tipifarnib-evoked cell death in U937 cells, whereas 2-APB potentiated this effect, demonstrating a link between tipifarnib-induced $Ca^{2+}$ influx and apoptosis. These results indicate tipifarnib causes cell death by dysregulating intracellular $Ca^{2+}$ homeostasis via activation of a plasma membrane $Ca^{2+}$ channel, and identify a novel mechanism for tipifarnib-induced cell death in hematological malignancies.

As such, a composition is disclosed comprising tipifarnib and 2-aminoethoxydiphenyl borate. The components of the composition may be used at a concentration or dose effective at treating a disease, such as leukemia. Accordingly, the tipifarnib may be used at between 100 nM and 10000 nM, or more specifically at between 100 nM and 10000 nM. In an alternative embodiment, tipifarnib is used at between 100-1, 200 mg bis in die (b.i.d.), or 400-1,200 mg b.i.d., or 600 mg b.i.d. Tipifarnib has been administered at 100 mg, 200 mg, 300 mg, 400 mg, 500 mg, 600 mg, 700 mg, 800 mg, 900 mg, 1,000 mg, 1,100 mg, and 1,200 mg. Likewise, 2-aminoethoxydiphenyl borate may be administered between 1 μM and 200 µM, or in alternative embodiments at 1-3 mg/kg. 2-aminoethoxydiphenyl borate has also been used at 2 mg/kg.

In additional embodiments, the composition also includes bortezomib. The bortezomib may be administered at 0.7-1.3 mg/m². In specific embodiments of the invention, the bortezomib is used at 1-1.3 mg/m².

Also disclosed is a method of treating cancer by evoking ER stress using a therapeutically effective amount of tipifarnib and administering a therapeutically effective amount of 2-aminoethoxydiphenyl borate concurrently. The components may be administered or dosed as described above. Additionally, a therapeutically effective amount of bortezomib may be administered.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

Figure 1:
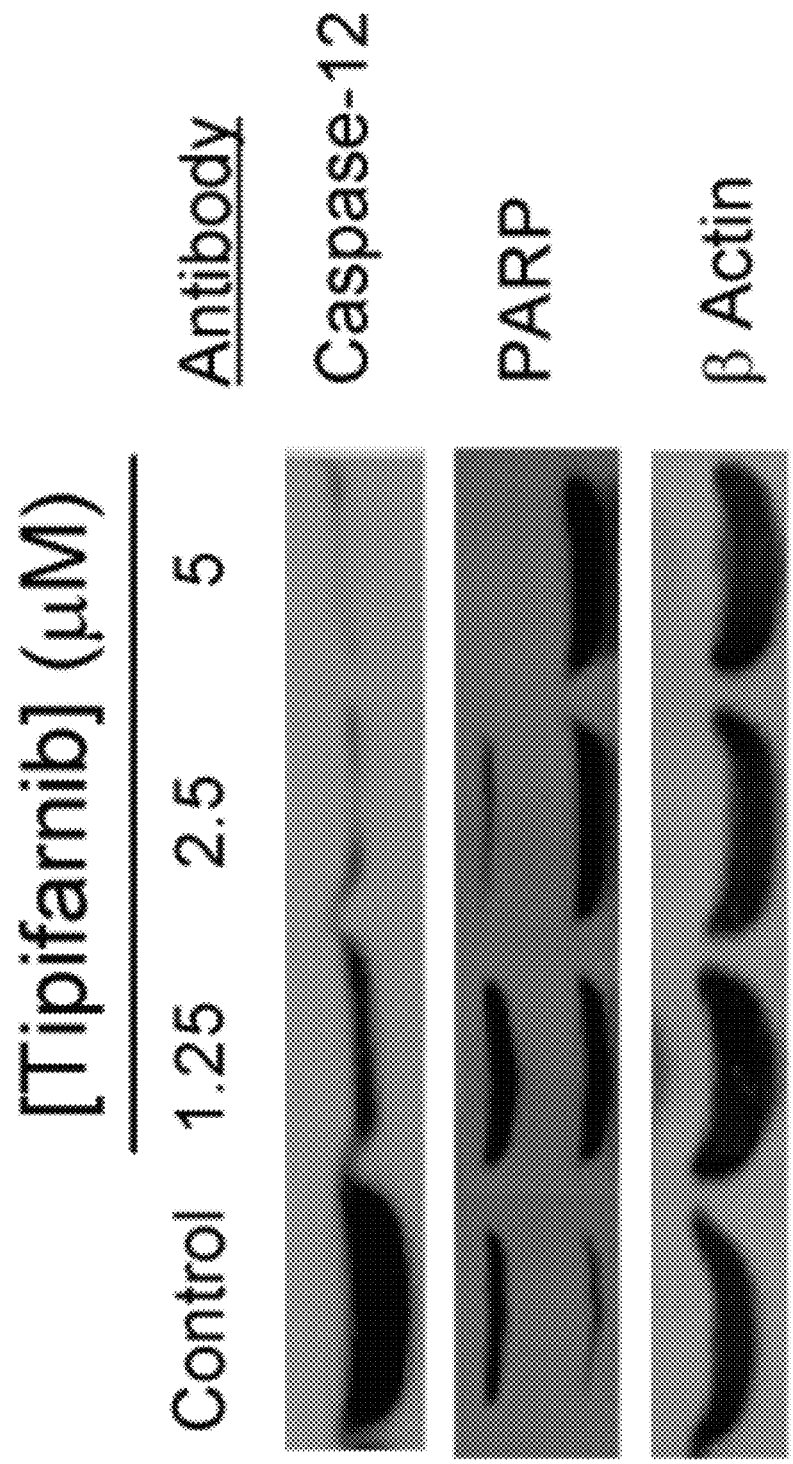
FIG. 1 is a western blot showing agents which evoke ER stress overcome cell adhesion mediated drug resistance in U937 cells. The blot analyzes protein extracts from U937 cells exposed to the indicated concentrations of tipifarnib and screened for cleaved caspase-12 and PARP, with β actin shown as a lane loading reference.

Tipifarnib is a FTI that has clinical activity in multiple myeloma and AML (Alsina M, et al. The farnesyltransferase inhibitor Zarnestra is well tolerated, induces stabilization of disease and inhibits farnesylation and oncogenic/tumor survival pathways in patients with advanced multiple myeloma. Blood2004; 103:3271-7, Karp J E, et al. Clinical and biologic activity of the farnesyltransferase inhibitor R115777 in adults with refractory and relapsed acute leukemias: a phase 1 clinical-laboratory correlative trial. Blood 2001; 97:3361-9). Interestingly, tipifarnib accumulates in bone marrow (Karp J E, et al. Clinical and biologic activity of the farnesyltransferase inhibitor R115777 in adults with refractory and relapsed acute leukemias: a phase 1 clinical-laboratory correlative trial. Blood 2001; 97:3361-9), a desirable property in hematopoietic malignancies that are dependent on the bone marrow microenvironment. As a single agent tipifarnib can overcome the CAM-DR phenotype in multiple myeloma and AML cell lines and primary isolates (data not shown). It had previously been reported that bortezomib shares similar activity in fibronectin-adhered (Mitsiades N, et al. The proteasome inhibitor PS-341 potentiates sensitivity of multiple myeloma cells to conventional chemotherapeutic agents: therapeutic applications. Blood 2003; 101:2377-80) and stroma-adhered (16) MM1s myeloma cells, The tipifarnib and bortezomib, alone and in combination, have activity not only in multiple myeloma and AML cells maintained in suspension culture, but also in tumor cells adhered to the extracellular matrix component fibronectin, seen in FIGS. 1 and 2(a)-(c), and indicate that tipifarnib combined with bortezomib effectively promote synergistic death and overcome de novo drug resistance (Yanamandra N, et al., Tipifarnib and bortezomib are synergistic and overcome cell adhesion-mediated drug resistance in multiple myeloma and acute myeloid leukemia. Clin Cancer Res 2006; 6:12, 591-599).

The present invention also encompasses a pharmaceutical composition useful in the treatment of cancer and oncogenic diseases, particularly leukemia, comprising the administration of a therapeutically effective amount of the compound of the present invention, with or without pharmaceutically acceptable carriers or diluents. The compositions of the present invention may further comprise one or more pharmaceutically acceptable additional ingredient(s) such as alum, stabilizers, antimicrobial agents, buffers, coloring agents, flavoring agents, adjuvants, and the like. The compositions of the present invention may be administered orally or parenterally including the intravenous, intramuscular, intraperitoneal, subcutaneous, rectal and topical routes of administration.

For oral use, the compositions of this invention may be administered, for example, in the form of tablets or capsules, powders, dispersible granules, or cachets, or as aqueous solutions or suspensions. In the case of tablets for oral use, carriers which are commonly used include lactose, corn starch, magnesium carbonate, talc, and sugar, and lubricating agents such as magnesium stearate are commonly added. For oral administration in capsule form, useful carriers include lactose, corn starch, magnesium carbonate, talc, and sugar. When aqueous suspensions are used for oral administration, emulsifying and/or suspending agents are commonly added.

In addition, sweetening and/or flavoring agents may be added to the oral compositions. For intramuscular, intraperitoneal, subcutaneous and intravenous use, sterile solutions of the active ingredient(s) are usually employed, and the pH of the solutions should be suitably adjusted and buffered. For intravenous use, the total concentration of the solute(s) should be controlled in order to render the preparation isotonic.

For preparing suppositories according to the invention, a low melting wax such as a mixture of fatty acid glycerides or cocoa butter is first melted, and the active ingredient is dispersed homogeneously in the wax, for example by stirring. The molten homogeneous mixture is then poured into conveniently sized molds and allowed to cool and thereby solidify.

Liquid preparations include solutions, suspensions and emulsions. Such preparations are exemplified by water or water/propylene glycol solutions for parenteral injection. Liquid preparations may also include solutions for intranasal administration. Aerosol preparations suitable for inhalation may include solutions and solids in powder form, which may be in combination with a pharmaceutically acceptable carrier, such as an inert compressed gas. Also included are solid preparations which are intended for conversion, shortly before use, to liquid preparations for either oral or parenteral administration. Such liquid forms include solutions, suspensions and emulsions.

The composition described herein may also be delivered transdermally. The transdermal compositions can take the form of creams, lotions, aerosols and/or emulsions and can be included in a transdermal patch of the matrix or reservoir type as are conventional in the art for this purpose.

The combinations of the present invention may also be used in conjunction with other well known therapies that are selected for their particular usefulness against the condition that is being treated.

Chemotherapeutic compounds used in this invention include Tipifarnib (Zarnestra; Johnson & Johnson Pharmaceutical Research and Development, LLC, Titusville, N.J.). Tipifarnib was dissolved in 100% DMSO (Sigma Chemical) and sonicated for 10 minutes at room temperature and was stored at −20° C. prior to use. Thapsigargin, tunicamycin, brefeldin A were obtained from EMD Biosciences (San Diego, Calif.). Calcium modulating agents, ruthenium red, lanthanum chloride, and 2-APB were obtained from Sigma (St. Louis, Mo.).

U937 cells were obtained from the American Type Culture Collection (ATCC) (Manassas, Va.) and maintained in RPMI 1640 media supplemented with 100 mM L-glutamine (Mediatech Inc., Herndon, Va.) and 10% fetal bovine serum (Omega Scientific Inc., Tarzana, Calif.).

Measurement of the Intracellular Calcium.

Intracellular free-calcium was measured using the calcium sensitive dye, fura-2 as previously described (DeHaven W I, Cuevas J. VPAC receptor modulation of neuroexcitability in intracardiac neurons: dependence on intracellular calcium mobilization and synergistic enhancement by PAC1 receptor activation. J Biol. Chem. 2004 Sep. 24; 279(39):40609-21). Cells were plated on coverslips coated with poly-d-lysine (Sigma), which enhances cell adhesion in the model and permits responses to chemotherapeutic agents in leukemia cell lines identical to those obtained with fibronectin (Landowski T H, et al. Mitochondrial-mediated disregulation of $Ca^{2+}$ is a critical determinant of Velcade (PS-341/bortezomib) cytotoxicity in myeloma cell lines. Cancer Res. 2005

May 1; 65(9):3828-36). Fura-2 loading was carried out incubating the plated cells for 1 hour at room temperature in physiological saline solution (PSS) consisting of (in mM): 140 NaCl, 3 KCl, 2.5 CaCl$_2$, 1.2 MgCl$_2$, 7.7 glucose and 10 HEPES (pH to 7.2 with NaOH), which also contained 1 μM of the membrane permeable ester form of fura-2, acetoxymethylester (fura-2 AM) fura-2 acetoxymethylester (fura-2 AM, +0.1% DMSO) and 0.1% dimethyl sulfoxide (DMSO). The coverslips were then washed in PSS (fura-2-AM free) prior to the experiments being carried out. All solutions were applied via a rapid application system identical to that previously described (Cuevas J, Berg D K. Mammalian nicotinic receptors with alpha7 subunits that slowly desensitize and rapidly recover from alpha-bungarotoxin blockade. J. Neurosci. 1998 Dec. 15; 18(24):10335-44).

A DG-4 high-speed wavelength switcher (Sutter Instruments Co., Novato, Calif.) was used to apply alternating excitation light, and fluorescent emission was captured using a Sensicam digital CCD camera (Cooke Corporation, Auburn Hills, Mich.) and recorded with Slidebook 3.0 software (Intelligent Imaging Innovations, Denver, Colo.). Changes in $[Ca^{2+}]_i$ were calculated using the Slidebook 3 software (Intelligent Imaging Innovations, Denver, Colo.) from the intensity of the emitted fluorescence following excitation with 340 and 380 nm light, respectively, using the Grynkiewicz equation:

$$[Ca^{2+}]_i = Kd\, Q\, (R-R_{min})/(R_{max}-R)$$

where R represents the fluorescence intensity ratio ($F_{340}/F_{380}$) as determined during experiments, Q is the ratio of $F_{min}$ to $F_{max}$ at 380 nm, and $K_d$ is the $Ca^{2+}$ dissociation constant for fura-2 (225 μM). The system was calibrated using a Fura-2 Calcium Imaging Calibration Kit (Molecular Probes; Eugene, Oreg.) and values for $F_{min}/F_{max}$, $R_{min}$, and $R_{max}$ were determined to be 23.04, 0.2, and 8.4, respectively.

Cytotoxicity Assays.

Cytotoxicity analysis was determined by using the 3-(4,5-dimethylthiazol-2-yl)-2,5-diphenyltetrazolium bromide (MTT) dye reduction assay as previously described (Damiano J S, et al. Cell adhesion mediated drug resistance (CAM-DR): role of integrins and resistance to apoptosis in human myeloma cell lines. Blood. 1999 Mar. 1; 93(5):1658-67). For all cytotoxicity studies cells were exposed to both calcium modulating agents and tipifarnib simultaneously for 72 hours. After 72 hours at 37° C., 50 μl of MTT (Sigma Chemical) was added to each well and cells were incubated for an additional four hours. Plates were spun for 5 minutes at 1200 rpm in a Sorvall RT6000D table top centrifuge (Asheville, N.C.), supernatants were removed, and water-insoluble product was dissolved in 100 μl of 100% DMSO. Plates were shaken for 30 seconds and absorbance read at 540 nm on a Wallac Victor-2 1420 Multilabel Counter (PerkinElmer, Torrance, Calif.). All experiments were done in triplicate.

Western Blotting.

Western blotting was performed as described previously (Beaupre D M, et al. Farnesyl transferase inhibitors enhance death receptor signals and induce apoptosis in multiple myeloma cells. Leuk Lymphoma. 2003 December; 44(12): 2123-34). Antibodies were purchased from the following vendors: caspase-12 (Abcam, Cambridge Mass.), poly adenosine triphosphate polymerase (Cell signaling, Boston Mass.), β-actin (Sigma Chemical). Briefly, after tipifarnib treatment cells were harvested by centrifugation, washed once with ice-cold PBS, and lysed in radioimmuno precipitation assay buffer (150 mM NaCl, 1 mM EGTA, 50 mM Tris-HCL [pH 7.5], 1% NP40, and 0.5% sodium deoxycholate) containing 0.2 mM phenylmethylsulfonyl fluoride, 56 ng/μl aprotinin, 10 ng/μl leupeptin, 1 ng/μl pepstatin, 1 mM Na$_3$VO$_4$, 1 mM NaF, and 10 mM Na$_4$P$_2$O$_7$. Then equal amounts of proteins were resolved on 10% SDS-polyacrylamide gels, transferred to polyvinylidene diflouride membrane (Bio-Rad, Hercules, Calif.), probed with the indicated antibody and developed using an enhanced chemiluminescence reagent (Amersham, Piscataway, N.J.).

Quantitative RT-PCR.

Total RNA was isolated from $2\times10^6$ log-phase 8226, 8226/R5 and U937 cells using the QIAshredder and RNeasy Mini Kits (Qiagen) according to the manufacturer's instructions. Reverse transcription and PCR was done using the Power SYBR Green RNA-to-C$_T$™ 1-step kit (Applied Biosystems) utilizing QuantiTect primers against Hs_GAPDH_2_SG and Hs_ORAI3_1_SG (Qiagen, QT01192646 and QT00231910 respectively) according to the manufacturer's instructions. Briefly, 4 ng total RNA was reacted in a 25 μl final volume using 1× final primer concentrations and recommended cycling specifications for SYBR Green on a StepOnePlus Real-Time PCR machine (Applied Biosystems). Reactions were performed in triplicate for target (ORAI3) and endogenous control (GAPDH) for each cell line. The experiment was repeated three times independently using freshly isolated RNA. All data was compiled and Relative quantity (RQ) of expression was calculated using the Applied Biosystems algorithm.

Statistical Analysis.

For multiple group comparisons, one-way or two-way analysis of the variance (ANOVA) tests were carried out, as appropriate. When the ANOVA indicated significant difference, a post-hoc analysis with the Tukey Test was conducted to identify the group or groups that were significantly different. Unless otherwise stated, statistical data are expressed as mean±standard error.

Example 1

Tipifarnib Administration Affects Calcium Levels

It has been shown that tipifarnib acts synergistically with bortezomib and can overcome cell adhesion-mediated drug resistance in multiple myeloma and acute myeloid leukemia. The capacity of tipifarnib to reverse the CAM-DR phenotype is believed to be due to induction of the ER stress response (Yanamandra N, et al. (2006) Tipifarnib and bortezomib are synergistic and overcome cell adhesion-mediated drug resistance in multiple myeloma and acute myeloid leukemia. *Clin Cancer Res* 12:591-599) in multiple myeloma and acute myeloid leukemia. Bortezomib dysregulates $[Ca^{2+}]_i$ thereby elicits ER stress and cytotoxicity in myeloma cells by inducing $Ca^{2+}$ from the mitochondria via a mechanism that appears to depend on the reversal of the mitochondrial $Ca^{2+}$ uniporter. (Landowski T H, et al. (2005) Mitochondrial-mediated disregulation of $Ca^{2+}$ is a critical determinant of Velcade (PS-341/bortezomib) cytotoxicity in myeloma cell lines. *Cancer Res* 65:3828-3836). Experiments were conducted to confirm that tipifarnib induces the ER stress response in leukemia cells using the acute myeloid leukemia cell line, U937. It has been shown that the bortezomib-induced $[Ca^{2+}]_i$ dysregulation and ensuing cytotoxicity are the result of $Ca^{2+}$ release from the mitochondria via reversal of the $Ca^{2+}$ uniporter (Landowski T H, et al. Mitochondrial-mediated disregulation of $Ca^{2+}$ is a critical determinant of Velcade (PS-341/bortezomib) cytotoxicity in myeloma cell lines. Cancer Res. 2005 May 1; 65(9):3828-36).

Leukemia cells were adhered onto fibronectin and treated with a total concentration of tipifarnib of 1.25, 2.5 or 5 μM for 48 hr. Protein extracts from untreated (Control) and tipifarnib treated U937 cells were probed for expression of procaspase-12, an ER resident caspase that is specifically activated by ER stress (Nakagawa T, et al. (2000) Caspase-12 mediates endoplasmic-reticulum-specific apoptosis and cytotoxicity by amyloid-beta. *Nature* 403:98-103).

As shown in FIG. 1, tipifarnib induced a dose dependent decrease in the levels of inactive caspase-12 protein. There is also a concomitant increase in degradation of the caspase-3 substrate, and the indicator of apoptosis, poly adenosine triphosphate polymerase (PARP). Incubation in tipifarnib also resulted in cleavage of caspase-4 (data not shown), a second caspase implicated in the ER stress response (Hitomi J, et al. (2004) Involvement of caspase-4 in endoplasmic reticulum stress-induced apoptosis and Abeta-induced cell death. *J Cell Biol* 165:347-356). Taken together, these data confirm that tipifarnib triggers ER-stress related pathways in leukemia cells.

Figure 3:
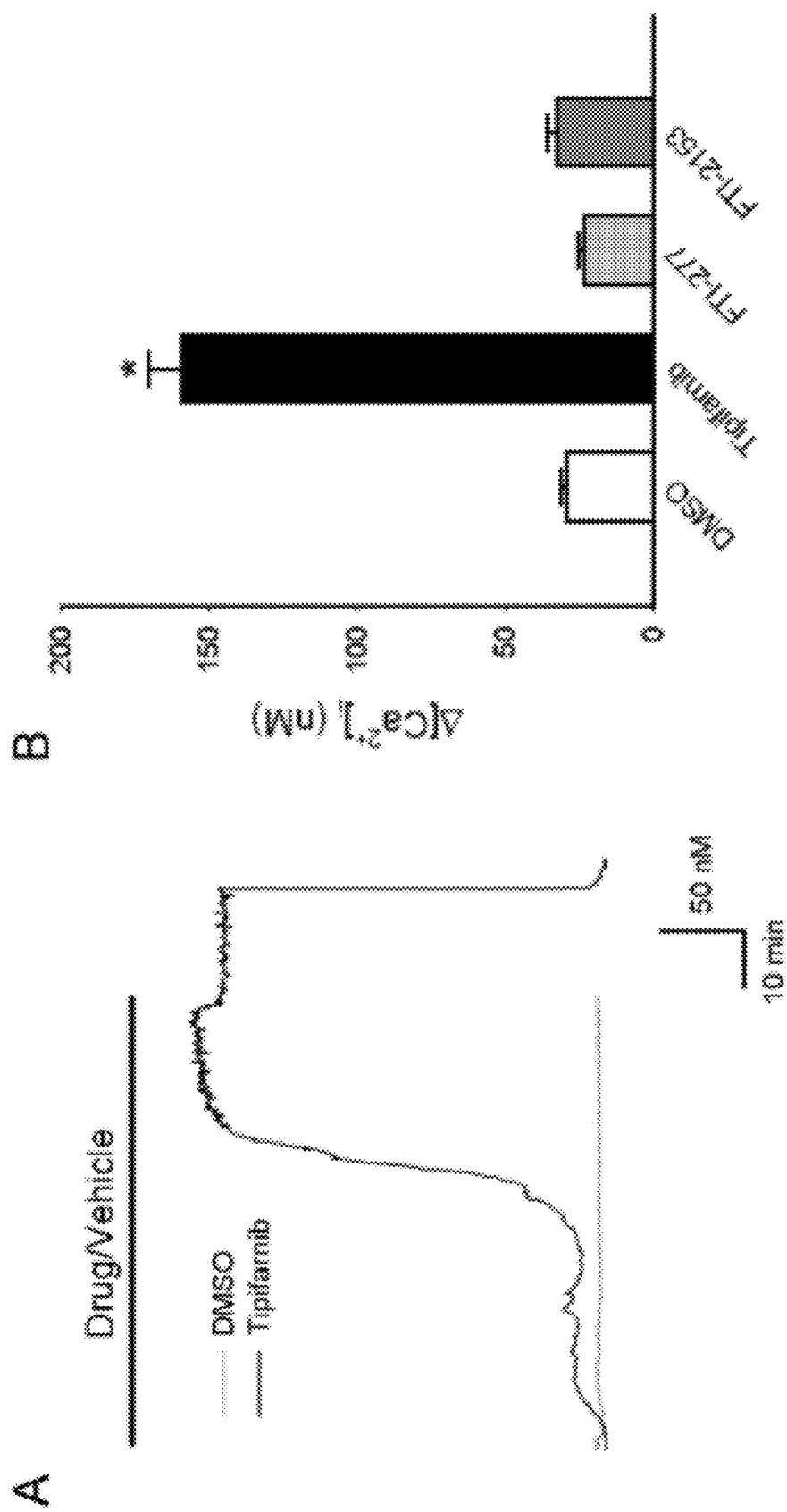
FIGS. 3(a)-(b) are graphs showing tipifarnib promotes $[Ca^{2+}]_i$ elevations in U937 cells. (A) Representative traces of $[Ca^{2+}]_i$ recorded from two U937 cells exposed to vehicle (DMSO) or 5 µM tipifarnib. Bar across top of traces indicates duration of DMSO or tipifarnib application. (B) Mean peak change in $[Ca^{2+}]_i$ ($\Delta[Ca^{2+}]_i$) observed in response to bath application of DMSO (n=40), 5 µM tipifarnib (n=67), 10 µM FTI-277 (n=49) or 10 µM FTI-2153 (n=49). Asterisk denotes significant difference from all other groups (p<0.001).

Dysregulation of intracellular $Ca^{+2}$ homeostasis is known to elicit ER stress. One of the key mechanisms by which non-excitable cells, such as hematopoetic cells, preserve ER $Ca^{2+}$ homeostasis is via SOC. These plasma membrane channels become activated when intra-ER $Ca^{2+}$ is depleted, and $Ca^{2+}$ influx through these SOC helps replenish ER $Ca^{2+}±$. The existence of these channels was first proposed by Dr. James Putney (Putney, J. W., Jr. A model for receptor-regulated calcium entry. (1986) *Cell Calcium* 1986 February; 7(1):1-12), and the best characterized of these store-operated currents is mediated by the $Ca^{2+}$-release activated $Ca^{2+}$ current ($I_{CRAC}$). Therefore, the effects of tipifarnib on intracellular $Ca^{2+}$ concentrations in tumor cells were studied in adhered U937 leukemic cells using fura-2 mediated $Ca^{2+}$ fluorometry. Application of 5 µM tipifarnib onto the U937 cells evoked pronounced elevations in the cytosolic $Ca^{2+}$ concentration ($[Ca^{2+}]_i$) when compared to vehicle (DMSO) treated U937 cells, seen in FIG. 3(a). The elevations in $[Ca^{2+}]_i$ occurred following a ~30 min incubation in tipifarnib and were not reversible upon washout of the drug. In some cells exposed to tipifarnib, the drug-induced elevations in $[Ca^{2+}]_i$ were followed by an apparent rapid decline in $[Ca^{2+}]_i$, seen in FIG. 3(a). The decrease in $[Ca^{2+}]_i$ was the result of a drop in signal at both the 340 nM and 380 nM wavelengths. Such declines in total fluorescence are indicative of a disruption in membrane integrity and likely, cell death, and were never observed in any of the vehicle treated cells. Increases in $[Ca^{2+}]_i$ in response to tipifarnib were significantly different (p<0.001) and more than 5-fold greater than the increases observed when vehicle alone (DMSO) was applied, as seen in FIG. 3(b).

Given that both tipifarnib and bortezomib can overcome CAM-DR, and that these drugs evoke ER stress (Yanamandra N, et al. Tipifarnib and bortezomib are synergistic and overcome cell adhesion-mediated drug resistance in multiple myeloma and acute myeloid leukemia. Clin Cancer Res. 2006 Jan. 15; 12(2):591-9; Landowski T H, et al. Mitochondrial-mediated disregulation of $Ca^{2+}$ is a critical determinant of Velcade (PS-341/bortezomib) cytotoxicity in myeloma cell lines. Cancer Res. 2005 May 1; 65(9):3828-36), experiments were conducted to determine if imperviousness to CAM-DR is an inherent property of agents which induce ER-stress. U937 leukemia cells were adhered to fibronectin and evaluated for sensitivity to the classical ER-stressors tunicamycin, thapsigargin and Brefeldin A. All of the tested ER-stressors induced a dose dependent increase in cell death in both suspension and fibronectin adhered tumor cells, seen in FIGS. 2(a)-(c). Importantly, there was no significant difference between the cellular viability induced in suspension or in adherent cells by any of the tested compounds in the concentration range tested. This observation indicates that fibronectin adherence does not protect tumor cells from ER-stress induced apoptosis.

Unlike tipifarnib, the peptidomimetic farnesyltransferase inhibitors FTI-277 and FTI-2153 failed to stimulate elevations in $[Ca^{2+}]_i$ at concentrations previously shown to have cellular effects (Lerner E C, et al. (1995) Ras CAAX peptidomimetic FTI-277 selectively blocks oncogenic Ras signaling by inducing cytoplasmic accumulation of inactive Ras-Raf complexes. *J Biol Chem* 270:26802-26806; Sun J, et al. (1999) Antitumor efficacy of a novel class of non-thiol-containing peptidomimetic inhibitors of farnesyltransferase and geranylgeranyltransferase I: combination therapy with the cytotoxic agents cisplatin, Taxol, and gemcitabine. *Cancer Res* 59:4919-4926), as seen in FIG. 3(b). Also, the loss of membrane integrity indicated by a sudden drop in fluorescence was not observed in any of the cells treated with FTI-277 and FTI-2153.

Figure 4:
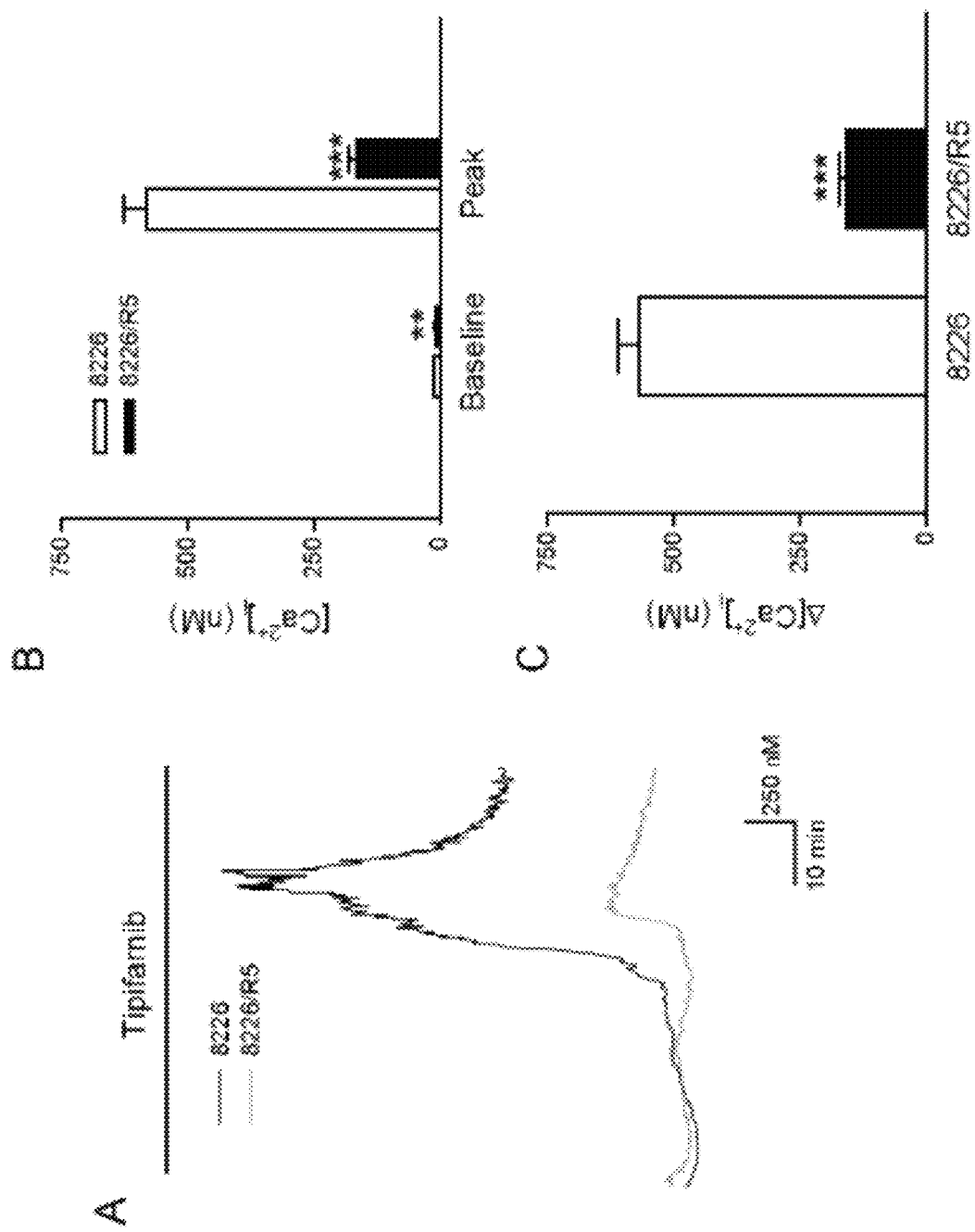
FIGS. 4(a)-(b) are graphs showing the tipifarnib-resistant cell line 8226/R5 shows decreased increases in $[Ca^{2+}]_i$ in response to the drug. (A) Representative traces of $[Ca^{2+}]_i$ recorded from an 8226 cell (black trace) and an 8226/R5 cell (gray trace) exposed to 5 µM tipifarnib. Bar across top of traces indicates duration of tipifarnib (5 µM) application. (B) Mean baseline and peak $[Ca^{2+}]_i$ observed in 8226 (n=177) and 8226/R5 (n=243) cells in response to bath application of 5 µM tipifarnib. Asterisks denote significant difference for baseline $[Ca^{2+}]_i$, (p<0.01) between 8226 and 8226/R5 cells and the peak (p<0.001) $[Ca^{2+}]_i$ observed when 5 µM tipifarnib (p<0.001) was applied to these cells lines. (C) Mean peak change in $[Ca^{2+}]_i$ produced by application of tipifarnib (5 µM) in 8226 (n=177) and 8226/R5 (n=243) cells. Asterisk indicates significant difference (p<0.001).

Experiments were carried out to determine if tipifarnib also promotes elevations in $[Ca^{2+}]_i$ in 8226 cells and in a tipifarnib resistant daughter cell line, 8226/R5. FIG. 4(a) shows representative responses obtained upon application of tipifarnib in the two cell types and demonstrates that tipifarnib elevated $[Ca^{2+}]_i$ to a greater extent in 8226 cells. The decrease in $[Ca^{2+}]_i$ observed in the 8226 cell was associated with a decrease in fura-2 fluorescence at both 340 nM and 380 nM excitation indicating that the cell was losing membrane integrity. In contrast, the decrease in fura-2 fluorescence in the 8226/R5 cell was due to a transient response in $[Ca^{2+}]_i$ to tipifarnib. Application of tipifarnib resulted in significantly greater increases in $[Ca^{2+}]_i$ in the 8226 cells, seen in FIG. 4(b). These elevations in $[Ca^{2+}]_i$ were sustained and often resulted in loss of membrane integrity. However, tipifarnib produced less pronounced and transient elevations in $[Ca^{2+}]_i$ in the resistant cell line, 8226/R5.

It has also been suggested that induction of the ER stress response by tipifarnib may be responsible for reversal of the CAM-DR phenotype (Yanamandra N, et al. Tipifarnib and bortezomib are synergistic and overcome cell adhesion-mediated drug resistance in multiple myeloma and acute myeloid leukemia. Clin Cancer Res. 2006 Jan. 15; 12(2):591-9). Experiments were conducted to confirm that tipifarnib induces the ER stress response in leukemia cells using the acute myeloid leukemia cell line, U937. Leukemia cells were adhered onto fibronectin and treated with 1.25, 2.5 or 5 µM tipifarnib for 48 hr. Protein extracts from untreated (Control) and tipifarnib treated U937 cells were probed for expression of procaspase-12, an ER resident caspase that is specifically activated by ER stress (Nakagawa T, et al. Caspase-12 mediates endoplasmic-reticulum-specific apoptosis and cytotoxicity by amyloid-beta. Nature. 2000 Jan. 6; 403(6765):98-103). As shown in FIG. 1, tipifarnib induced a dose dependent decrease in the levels of inactive caspase-12 protein, and a concomitant increase in degradation of the caspase-3 substrate, and the indicator of apoptosis, poly adenosine triphosphate polymerase (PARP). Incubation in tipifarnib also resulted in cleavage of caspase-4, a second caspase implicated in the ER stress response (data not shown) (Hitomi J, et al. Involvement of caspase-4 in endoplasmic reticulum stress-induced apoptosis and Abeta-induced cell death. J. Cell Biol. 2004 May 10; 165(3):347-56). Taken together, these data confirm that tipifarnib triggers ER-stress related pathways in leukemia cells.

Example 2

Tipifarnib Evokes Plasmalemmal $Ca^{2+}$ Influx but not $Ca^{2+}$ Release from Intracellular Stores Tipifarnib has been shown to promote apoptosis in several models of hematopoietic malignancies, including the multiple myeloma cell line 8226 (Buzzeo R, et al. (2005) Characterization of a R115777-resistant human multiple myeloma cell line with cross-resistance to PS-341. *Clin Cancer Res* 11:6057-6064). ER stress can be induced by various factors such as disruption of intracellular $Ca^{2+}$ homeostasis, such as that produced by thapsigargin, inhibition of protein glycosylation, such as that evoked by tunicamycin, or other causes, including oxidative stress and accumulation of misfolded proteins in the ER (Rao R V, et al. Coupling endoplasmic reticulum stress to the cell death program. Cell Death Differ. 2004 April; 11(4):372-80).

Figure 2:
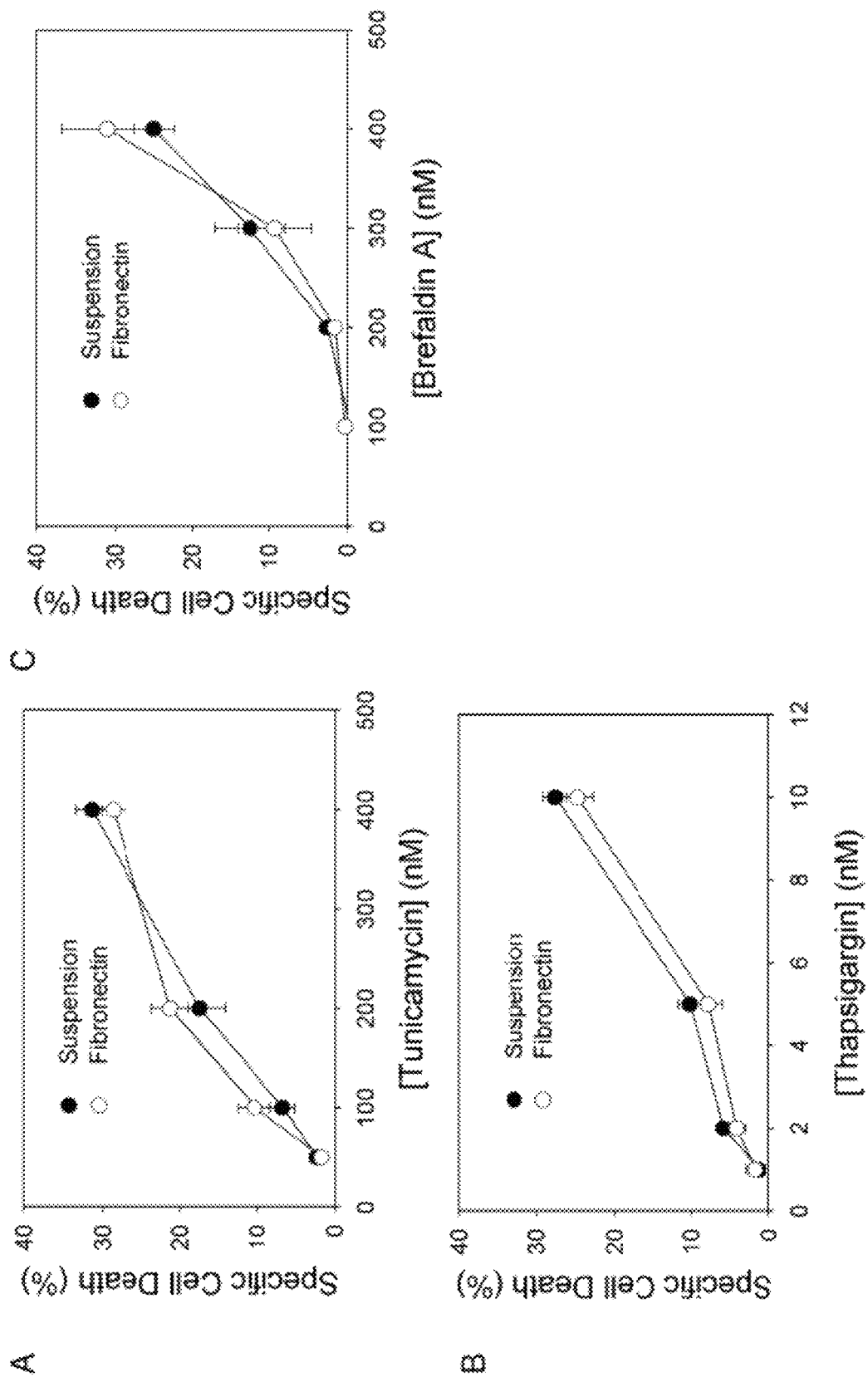
FIGS. 2(a)-(c) are graphs showing agents which evoke ER stress overcome cell adhesion mediated drug resistance in U937 cells. Percent of specific cell death induced in U937 cells in suspension (Suspension) or following adhesion to plates coated in fibronectin (Fibronectin) as a result of incubation in (A) tunicamycin, (B) thapsigargin, or (C) brefeldin A at the indicated concentrations.

It was unknown whether tipifarnib acts via an identical mechanism as bortezomib to induce cell death and act synergistically with bortezomib, or if the FTI is targeting a second molecular mechanism which also culminates in the induction of ER stress and concomitant cell death. Experiments were carried out to determine if tipifarnib alters $[Ca^{2+}]_i$ in hematological tumor cells via a similar mechanism. FIG. 2(a) shows representative traces of $[Ca^{2+}]_i$ recorded from cells in response to application of tipifarnib (Control) or when tipifarnib was applied following preincubation (1 hr) in ruthenium red (100 nM), an inhibitor of the mitochondrial $Ca^{2+}$ uniporter. Preincubation in ruthenium red failed to inhibit the tipifarnib-induced $Ca^{2+}$ elevation, and resulted in increases in $[Ca^{2+}]_i$ that were greater than those observed in control cells (tipifarnib alone). Similarly, depletion of intracellular $Ca^{2+}$ stores with the sarcoplasmic/endoplasmic $Ca^{2+}$-ATPase inhibitor, thapsigargin, did not inhibit the elevations in $[Ca^{2+}]_i$ elicited by tipifarnib. In identical experiments, preincubation in ruthenium red resulted in a statistically significant increase in the $[Ca^{2+}]_i$ elevations evoked by tipifarnib, whereas thapsigargin had no effect on these changes in $[Ca^{2+}]_i$. Taken together, the data indicate that the mechanism by which tipifarnib increases $[Ca^{2+}]_i$ in U937 cells does not involve liberation of $Ca^{2+}$ from intracellular pools. Furthermore, mitochondrial uptake of $Ca^{2+}$ mitigates these $[Ca^{2+}]_i$ elevations, and inhibition of the mitochondrial $Ca^{2+}$ uniporter by ruthenium red exacerbates the intracellular $Ca^{2+}$ dysregulation elicited by tipifarnib.

Figure 5:
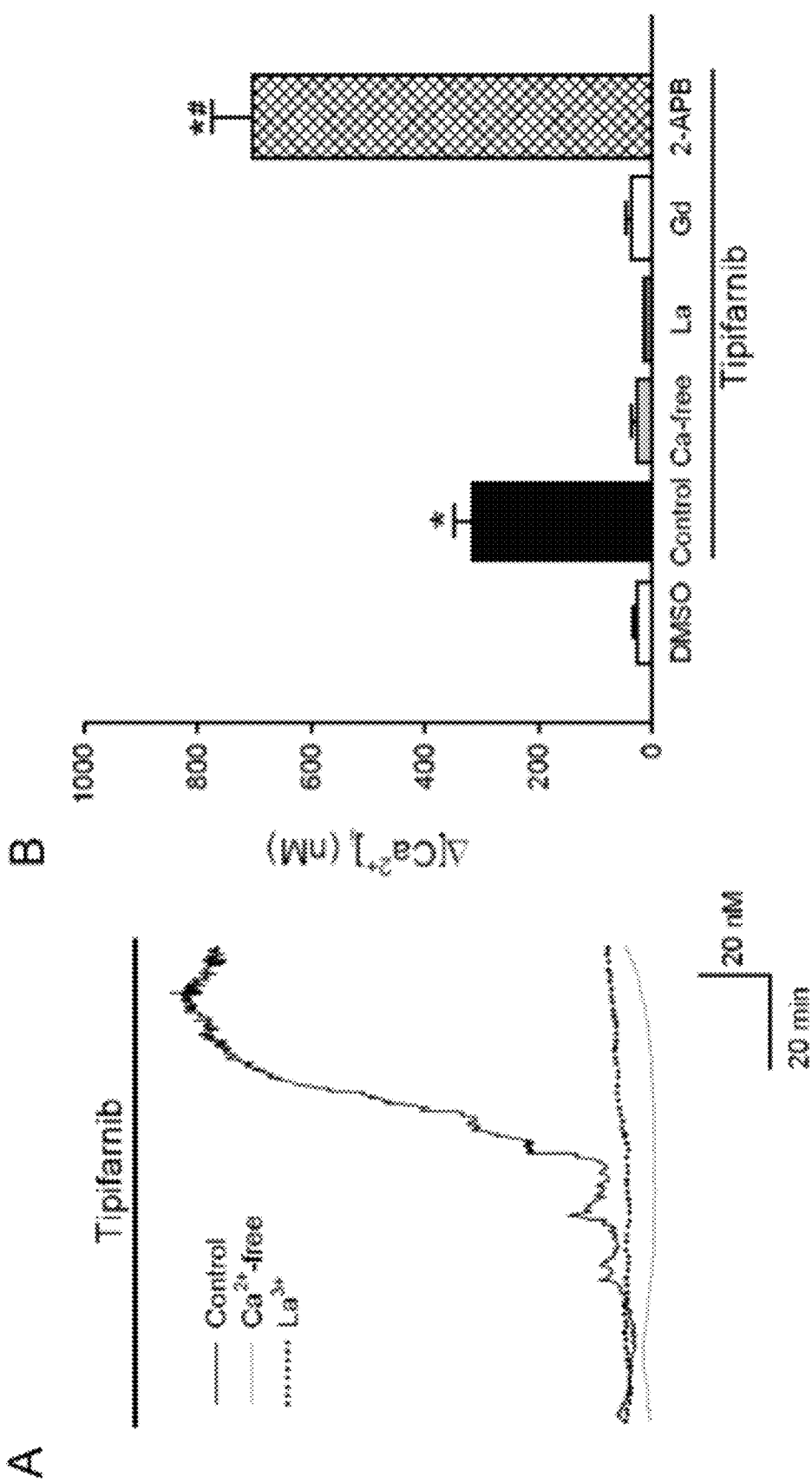
FIGS. 5(a)-(b) are graphs showing tipifarnib evokes $Ca^{2+}$ influx through the plasma membrane of U937 cells. (A) Representative traces of $[Ca^{2+}]_i$ recorded from three U937 cells in response to tipifarnib (5 µM) in normal physiological saline solution (PSS) (Control) or PSS with nominal $Ca^{2+}$ ($Ca^{2+}$-free) or when tipifarnib (5 µM) was applied in PSS containing 100 nM $La^{3+}$ ($La^{3}\pm$). (B) Bar graph of mean peak increases in $[Ca^{2+}]_i$ evoked by vehicle control (DMSO, n=52) or 5 µM tipifarnib in normal PSS (Control, n=29) or PSS with nominal $Ca^{2+}$ ($Ca^{2+}$-free, n=37), 100 nM $La^{3+}$ (La, n=6), 100 µM $Gd^{3+}$ (Gd, n=9), or 100 µM 2-APB (2-APB, n=21). Asterisks denote significant difference from DMSO (p<0.05) and pound symbol indicates significant difference from tipifarnib control group (Control, p<0.001).

To determine if tipifarnib elevates $[Ca^{2+}]_i$ by promoting an influx of $Ca^{2+}$ into leukemia cells, experiments were carried out whereby tipifarnib was applied in the absence and presence of extracellular $Ca^{2+}$ (2.5 mM) and in the presence of $Ca^{2+}$ and the pan-selective $Ca^{2+}$ channel inhibitors $La^{3+}$ (10 μM) and $Gd^{3+}$ (100 μM). FIG. 5(a) shows representative traces of $[Ca^{2+}]_i$ recorded from U937 cells exposed to tipifarnib under the indicated conditions. U937 cells failed to exhibit increases in $[Ca^{2+}]_i$ in response to tipifarnib when either extracellular $Ca^{2+}$ was removed from the bath solution or when 10 μM $La^{3+}$ was applied along with the drug. In similar experiments, both depletion of extracellular $Ca^{2+}$ or application of $La^{3+}$ depressed the tipifarnib-induced elevations in $[Ca^{2+}]_i$ in a statistically significant manner, seen in FIG. 5(b). A second pan-selective $Ca^{2+}$ channel blocker, $Gd^{3+}$ (100 μM), also blocked the effects of tipifarnib, seen in FIG. 5(b).

Figure 6:
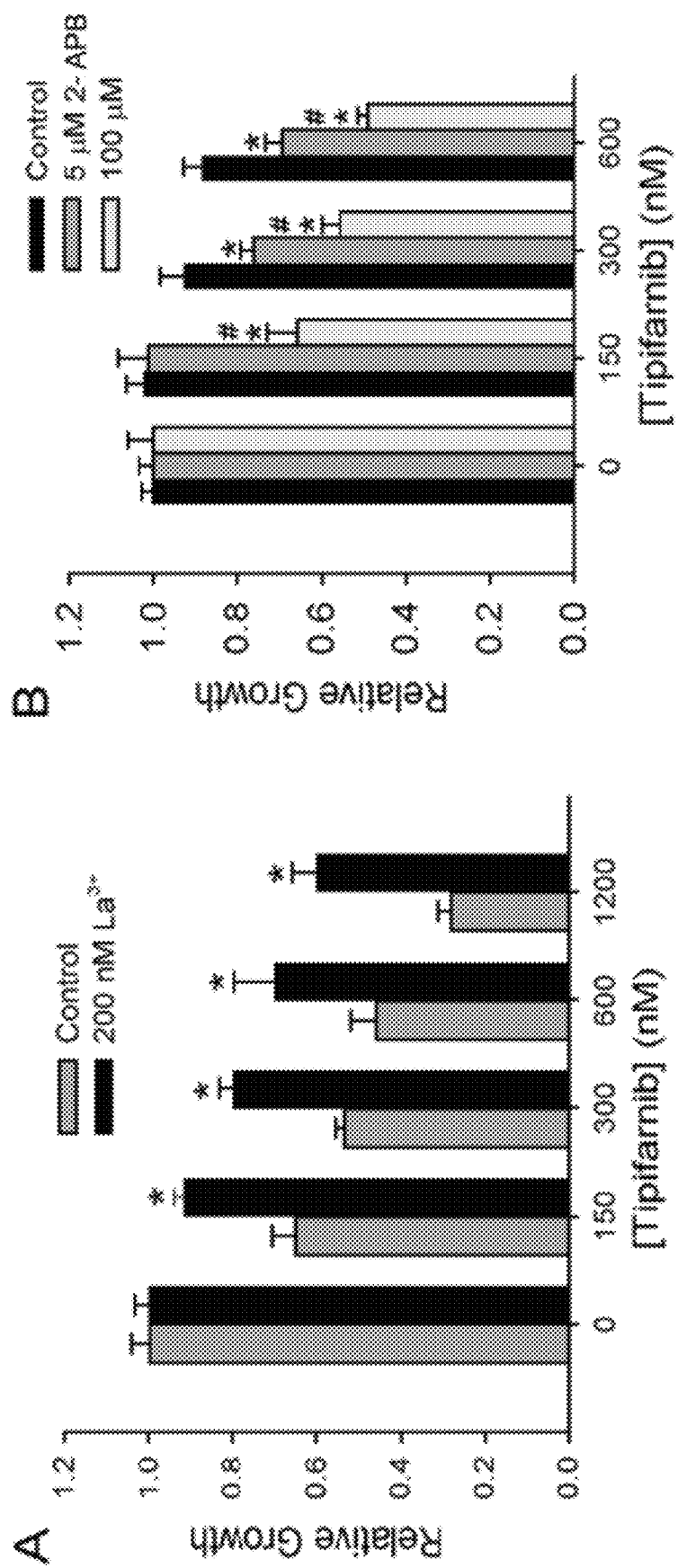
FIGS. 6(a)-(b) are graphs showing $La^{3+}$, but not 2-APB, inhibits tipifarnib-induced growth suppression of U937 cells. (A) Mean±SE growth rate of U937 cells, normalized to control (no tipifarnib), observed for the indicated concentrations of tipifarnib in the absence (Control) and presence of 200 nM $La^{2+}$. (B) Bar graph of mean growth rate of U937 cells, normalized to control (no tipifarnib), observed for increasing concentrations of tipifarnib in the absence (Control) and presence of 2-APB at the indicated concentrations. Asterisks in (A) and (B) denote significant difference from control group at each tipifarnib concentration (p<0.05), and pound symbols in (B) indicate significant difference from 5 µM 2-APB (p<0.05). For all groups n=3.

The effects of the $Ca^{2+}$ channel inhibition, using $La^{3+}$ and $Gd^{3+}$, were tested on survival of U937 cells. FIG. 6(a) shows a bar graph of the relative growth rate of U937 cells as a function of tipifarnib concentration in the absence and presence of 200 nM $La^{3+}$ as determined using an 3-(4,5-dimethylthiazol-2-yl)-2,5-diphenyltetrazolium bromide (MTT) cytotoxicity assay. Application of $La^{3+}$ provided a statistically significant increase in survival of U937 cells at all tipifarnib concentrations tested. Thus, inhibition of the tipifarnib-induced increase in $[Ca^{2+}]_i$ was associated with a statistically significant increase in the survival of U937 cells.

Similar protection from tipifarnib-induced growth inhibition was observed with co-application of $Gd^{3+}$ (100 but not with ruthenium red (100 nM) (data not shown). Thus, the results imply that the increases in $[Ca^{2+}]_i$ produced by tipifarnib contribute to the tumor cell death elicited by this drug.

Three $La^{3+}$- and $Gd^{3+}$-sensitive $Ca^{2+}$ channel subtypes have been identified in U937 cells, TRPM2, TRPM7 and the $Ca^{2+}$ release-activated $Ca^{2+}$ channel ($I_{CRAC}$) (Wu S N, et al. (1997) Characteristics of store-operated Ca(2+)-permeable current in monocytic U937 cells. *Chin J Physiol* 40:115-120; Lee Y K, et al. (2006) Characterization of $Ca^{2+}$ influx induced by dimethylphytosphingosine and lysophosphatidylcholine in U937 monocytes. *Biochem Biophys Res Commun* 348: 1116-1122). To gain insight into the specific ion channels mediating the tipifarnib-induced growth inhibition 2-APB was tested at concentrations which differentially affect TRPM2, TRPM7 and $I_{CRAC}$. At 5 μM, 2-APB activates $I_{CRAC}$, but at 100 this drug blocks both TRPM7 and $I_{CRAC}$; however, neither concentration of 2-APB affects TRPM2 channels. FIG. 6(b) shows a bar graph of the relative growth rate of U937 cells as a function of tipifarnib concentration in the absence and presence of 2-APB at the indicated concentrations. Both low (5 μM) and high (100 μM) concentrations of 2-APB failed to prevent tipifarnib-evoked effects on cell survival, but conversely, enhanced cell death.

Activation of the store-operated calcium channels (SOC) expressed in these cells, however, has not been linked to cell death. On the contrary, inhibition of these channels is associated with decreased cell proliferation in response to ATP and low levels of thapsigargin (Willmott N J, et al. Functional importance of the dihydropyridine-sensitive, yet voltage-insensitive store-operated $Ca^{2+}$ influx of U937 cells. FEBS Lett. 1996 Sep. 30; 394(2):159-64). Moreover, while the inhibition of tipifarnib-induced $Ca^{2+}$ influx by $La^{3+}$ and $Gd^{3+}$ is consistent with a SOC-mediated phenomenon, the lack of sensitivity to 2-APB is not. SOC are known to be potentiated by low levels of 2-APB ($\leq 5$ μM) and inhibited by higher levels of the drug. Thus, 100 μM 2-APB would have blocked tipifarnib-induced $Ca^{2+}$ influx if this effect was mediated by SOC, but the results show that 100 μM 2-APB potentiated this $Ca^{2+}$ entry. The enhanced tipifarnib suppression of cell growth seen here in the presence of 2-APB may in part be due to inhibition of SOC by 100 μM 2-APB. Alternatively, 2-APB may be further promoting cell death by increasing $Ca^{2+}$ influx when co-applied with tipifarnib. Further, TRPM2 expressed in HEK-293 cells showed that the channels are not blocked by 2-APB even at a concentration of 150 μM (Xu S Z, et al. Block of TRPCS channels by 2-aminoethoxydiphenyl borate: a differential, extracellular and voltage-dependent effect. Br J. Pharmacol. 2005 June; 145(4):405-14). However, 100 μM 2-APB which blocks various plasma membrane $Ca^{2+}$ channels, including store-operated $Ca^{2+}$ channels, did not prevent tipifarnib-induced increases in $[Ca^{2+}]_i$. On the contrary, when 2-APB was co-applied with tipifarnib, the increases in $[Ca^{2+}]_i$ were more pronounced than with tipifarnib alone, seen in FIG. 5(b).

The mechanisms by which tipifarnib induces ER stress and apoptosis in an acute myeloid leukemia model, U937 cells, show that tipifarnib dysregulates intracellular calcium in a mitochondrial- and ER-independent manner in these cells. Tipifarnib-induced disruption of intracellular $Ca^{2+}$ homeostasis, ER stress, and apoptosis was found to involve activation of a plasma membrane $Ca^{2+}$ channel.

Tipifarnib-resistant 8226 myeloma cells express high levels of calcium signaling pathway proteins (Buzzeo R, et al. Characterization of a R115777-resistant human multiple myeloma cell line with cross-resistance to PS-341. Clin Cancer Res. 2005 Aug. 15; 11(16):6057-64), raising the possibility that tipifarnib-induced ER stress is also the result of dysregulation of intracellular calcium homeostasis. The effects of tipifarnib on intracellular calcium concentrations in tumor cells were studied in adhered U937 leukemic cells using fura-2 mediated $Ca^{2+}$ fluorometry. Application of 5 µM tipifarnib onto the U937 cells evoked pronounced elevations in the cytosolic $Ca^{2+}$ concentration ($[Ca^{2+}]_i$) when compared to vehicle (DMSO) treated U937 cells, seen in FIG. 3(a). The elevations in $[Ca^{2+}]_i$ occurred following a ~30 min incubation in tipifarnib and were not reversible upon washout of the drug. In some cells exposed to tipifarnib, seen in FIG. 3(a), the drug-induced elevations in $[Ca^{2+}]_i$ were followed by an apparent rapid decline in $[Ca^{2+}]_i$. The decrease in $[Ca^{2+}]_i$ was the result of a drop in signal at both the 340 nM and 380 nM wavelengths. Such declines in total fluorescence are indicative of a disruption in membrane integrity and likely, cell death, and were never observed in any of the vehicle treated cells. Increases in $[Ca^{2+}]_i$ in response to tipifarnib were significantly different ($p<0.001$) and more than 5-fold greater than the increases observed when vehicle alone (DMSO) was applied, seen in FIG. 3(b). Unlike tipifarnib, the peptidomimetic farnesyl transferase inhibitors FTI-277 and FTI-2153 failed to stimulate elevations in $[Ca^{2+}]_i$ at concentrations previously shown to have cellular effects (Sun J, et al. Antitumor efficacy of a novel class of non-thiol-containing peptidomimetic inhibitors of farnesyltransferase and geranylgeranyltransferase I: combination therapy with the cytotoxic agents cisplatin, Taxol, and gemcitabine. Cancer Res. 1999 Oct. 1; 59(19):4919-26; Lerner E C, et al. Ras CAAX peptidomimetic FTI-277 selectively blocks oncogenic Ras signaling by inducing cytoplasmic accumulation of inactive Ras-Raf complexes. J Biol. Chem. 1995 Nov. 10; 270(45):26802-6), seen in FIG. 3(b). Also, the loss of membrane integrity indicated by a sudden drop in fluorescence was not observed in any of the cells treated with FTI-277 and FTI-2153.

Example 3

Characterization of SOC Channels

Recently, there has been a drive to identify biomarkers that will facilitate prediction of positive outcomes for the use of specific therapeutics in multiple myeloma. Data indicate that 8228, H929 and U937 cells express SOC with biophysical and/or pharmacological characteristics consistent with Orai1-and Orai3-containing channels. The biophysical and pharmacological properties of SOC are poorly understood in MM cells and a basic understanding is fundamental to facilitate screening these channels as a biomarker and target for pharmacotherapy in MM.

Therefore, SOC biomarkers were identified and characterized. The SOC channels are examined to determine how tipifarnib alters these properties, and how modifying Orai-SOC activity ultimately affects the cells. The store-operated $Ca^+$ channel (SOC) constituent, Orai3, is seen expressed at high levels in multiple myeloma cells and that activation of this channel by tipifarnib can be used to effectively treat multiple myeloma.

One of the most interesting observations made was that 2-APB potentiated the effects of tipifarnib on $[Ca^{2+}]_i$ in tipifarnib-insensitive 8226/R5 cells, such that these responses were comparable to those obtained with tipifarnib alone in tipifarnib-sensitive 8226 cells. However, it remains to be established if enhanced increase of $[Ca^{2+}]_i$ translates to greater efficacy of tipifarnib as an antiproliferative agent. Conducting cell growth (MTT) and cell death (annexin V) assays using a protocol similar to those described above illustrates whether 2-APB can enhance tipifarnib-induced cell death, using H929, 8226 and 8226/R5 cells. The ability of 2-APB to potentiate tipifarnib-induced increases in $[Ca^{2+}]_i$ was also tested using the same protocol described above.

SOC-mediated elevations in intracellular $Ca^{2+}$ and membrane currents were recorded in 8226, 8226/R5 and H929 in the absence and presence of tipifarnib (1 nM-5 µM). In cells exposed to tipifarnib, once the intracellular $Ca^{2+}$ response has reached plateau, seen in FIG. 3(a), after the initial exposure to $Ca^{2+}$, the cells were washed in DVF for 10 min and $Ca^{2+}$ containing solution reapplied in the absence and presence of the drug to be tested. DVF. The calcium kinetics are used as an indicator of SOC inactivation. $Ca^{2+}$ imaging experiments the protocol were used to determine both the state of intracellular store $Ca^{2+}$ loading and SOCE. The drugs tested (and concentration range) are: SKF-96365 (1-100 µM), 2-APB (1 µM-100 µM), $Gd^{3+}$ and $La^{3+}$ (10 nM-100 µM). This combination of drugs is sufficient to differentiate between $I_{CRAC}$, non-$I_{CRAC}$ SOC, and other $Ca^{2+}$ channel types (Parekh A B and Putney J W, Jr. (2005) Store-operated calcium channels. *Physiol Rev* 85:757-810). The data indicate that there is little to no run-down in the $Ca^{2+}$ responses between the first and second exposure to $Ca^{2+}$, and thus any observed effects are likely due to drug actions on the channels. The lack of specific inhibitors of SOCs is well-documented, thus the compounds available are limited.

Figure 7:
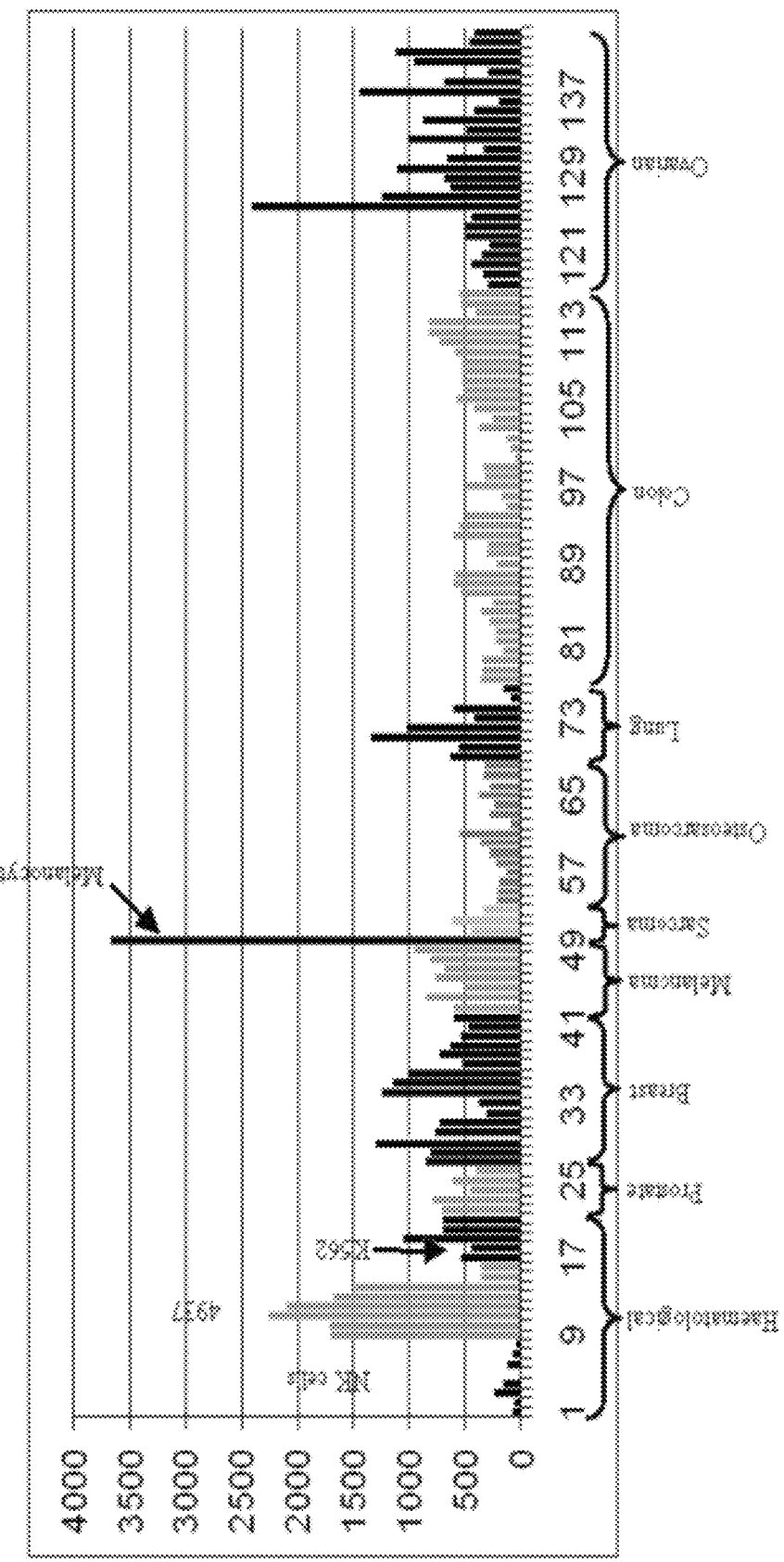
FIG. 7 is a graph showing store-operated calcium component ORAI3 levels in different oncogenic cell lines.
Figure 8:
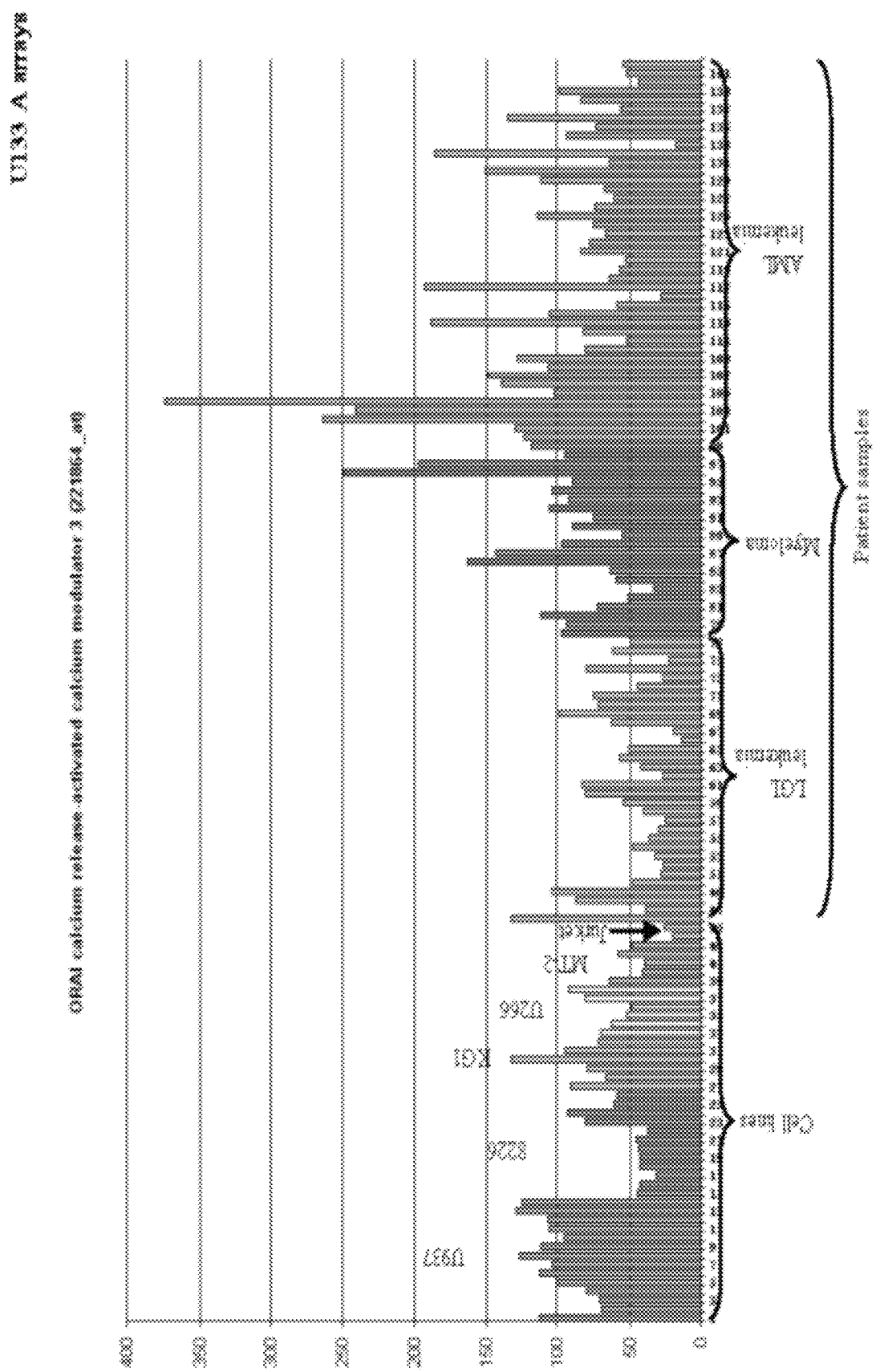
FIG. 8 is a graph showing store-operated calcium component ORAI3 levels in cell lines and patient cancer cells.

Orai3 differs from Orai1 and Orai2 in that it is equally potentiated by the three divalent cations, whereas Orai1 and Orai2 are preferentially potentiated by $Ca^{2}±$. It is important to note that the use of the 8226/R5 is a critical control used throughout these studies, since 8226/R5 cells have proven to be more resistant to tipifarnib than the parent cell line (Buzzeo R, et al. (2005) Characterization of a R115777-resistant human multiple myeloma cell line with cross-resistance to PS-341. *Clin Cancer Res* 11:6057-6064). Further, testing of various oncogenic cell lines indicates that ORAI3 is elevated in cancer cells, seen in FIGS. 7 and 8. Thus, cells likely have compromised SOC activity whereas H929 cells have enhanced SOC activity, as seen in FIGS. 9(a)-(c).

The extent to which tipifarnib activates SOC was determined by comparing SOC activity (defined by current potentiation by DVF solution) immediately after electrical access was achieved in the absence and presence of the FTI. With passive activation of SOC there is a ~5 min delay in activation of SOC, permitting this comparison (Bird G S, et al. (2008) Methods for studying store-operated calcium entry. *Methods* 46:204-212). The effect of tipifarnib on maximal SOC current amplitude was determined by comparing the SOC currents in the absence and presence of tipifarnib 10 min after the whole-cell configuration was established. In addition, the ability of tipifarnib to affect both fast and slow $Ca^{2+}$-dependent inactivation of SOC was analyzed. Of the three Orai subtypes, Orai3 exhibits the strongest fast $Ca^{2+}$-dependent inactivation, whereas Orai1 is the only subunit affected by slow $Ca^{2+}$-dependent inactivation. To examine fast $Ca^{2+}$-dependent inactivation, cells were held at 0 mV, and 2 s voltage steps to −80 mV applied.

Figure 9:
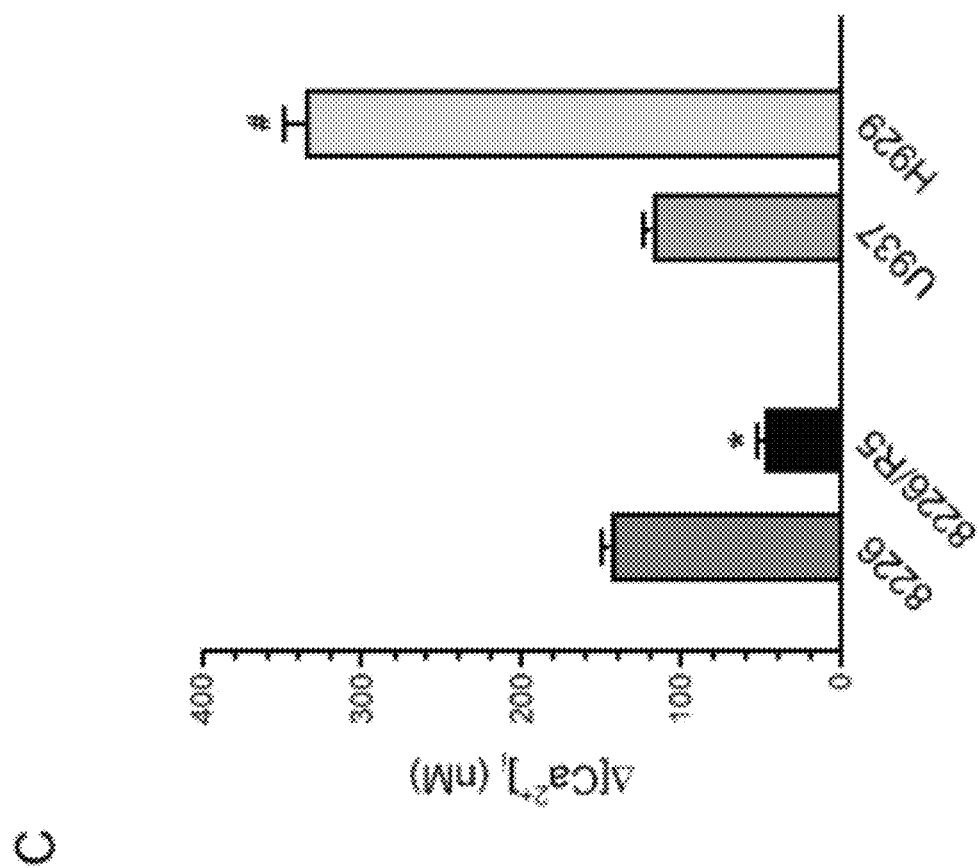
FIGS. 9(a)-(c) are graphs showing store-operated calcium entry in leukemia cell lines. Representative traces of $\Delta[Ca^{2+}]_i$ as a function of time recorded from (A) 8226 and 8226/R5 cells or (B) U937 and H929 cells. (C) Bar graph of mean maximal changes in $[Ca^{2+}]_i$ (±SEM) in response to adding back external $Ca^{2+}$ recorded from the indicated cell lines (n>9 for all). Asterisk and pound symbols denote significant difference from 8226 cells and all cells, respectively (p<0.001).
Figure 9:
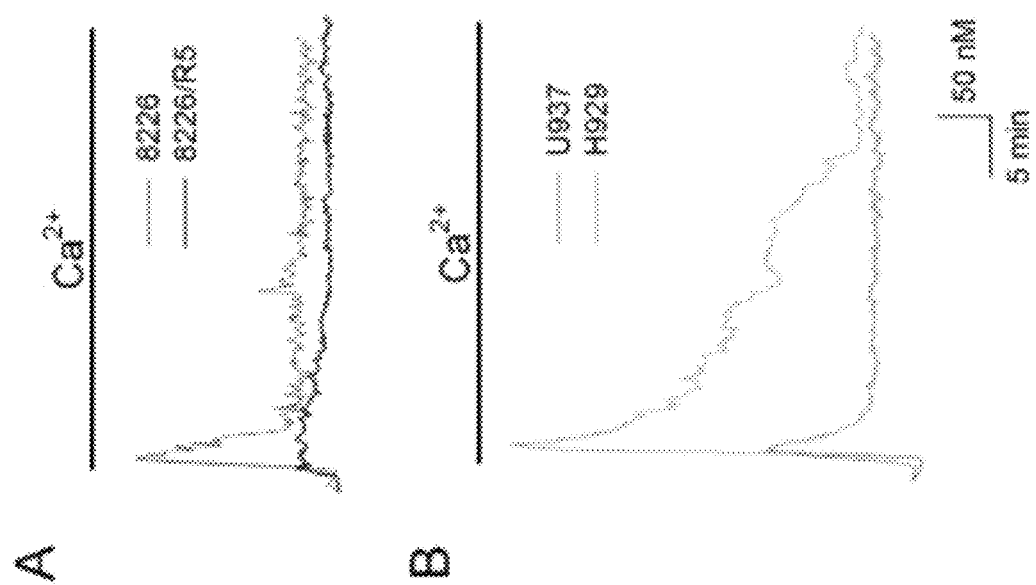

Cell lines which exhibit sensitivity and resistance to tipifarnib, 8226 and 8226/5R cells, respectively, show robust elevations in $[Ca^{2+}]_i$ in 8226 cells following application of 5 µM tipifarnib, seen in the representative $[Ca^{2+}]_i$ traces of FIG. 9(a). Increases in $[Ca^{2+}]_i$ noted for 8226/R cells were not as pronounced. Furthermore, 8226 cells, like U937 cells, displayed apparent rapid decreases in $[Ca^{2+}]_i$ that were associated with loss of fura-2 florescence, which is indicative of compromised plasma membrane integrity. In contrast, 8226/

R5 cells displayed transient increases in $[Ca^{2+}]_i$ following tipifarnib application, but the decrease in $[Ca^{2+}]_i$ were not due to a loss of fura-2 fluorescence. Similar experiments showed that 8226/R5 cells had baseline $[Ca^{2+}]_i$ which was lower than the parent 8226 cell line, and they exhibited significant lower $[Ca^{2+}]_i$ increases in response to 5 µM tipifarnib, as seen in FIG. 9(b). The change in $[Ca^{2+}]_i$ evoked by 5 µM tipifarnib in 8226 cells was >250% greater than that observed in 8226/R5 cells, as seen in FIG. 9(c).

Important from a therapeutic standpoint, drug efflux pumps such as MDR-associated protein (MRP) and the P-glycoprotein have little influence on the efficacy of drugs acting on the extracellular domain of Orai3 containing channels. One of the major causes of treatment failures in relapse multiple myeloma is the development of multi-drug resistance (Tucci M, et al. (2009) Role of active drug transporters in refractory multiple myeloma. *Curr Top Med Chem* 9:218-224). While the resistance to specific chemotherapeutic agents is a complicated process involving numerous factors, such as selection of cells with altered levels of the molecule(s) targeted by a specific agent, both MRP and P-glycoprotein confer simultaneous resistance to multiple chemically unrelated anticancer agents to MM cells (Tucci M, et al. (2009) Role of active drug transporters in refractory multiple myeloma. *Curr Top Med Chem* 9:218-224). These plasma membrane pumps evoke the efflux of chemotherapeutic agents from the cell, which result in sub-toxic cellular levels of the compounds and compromised drug effectiveness. Modulators of MDR1 have been developed to counteract the effects of this transporter, but the clinical results are poor, primarily due to drug toxicity (Mayur Y C, et al. (2009) Design of new drug molecules to be used in reversing multi-drug resistance in cancer cells. *Curr Cancer Drug Targets* 9:298-306). Thus, an agent such as tipifarnib, which appears to act on an extracellular site, possesses distinct advantages over drugs that need to penetrate the cell to exert their effects.

Example 4

Co-Administering Tipifarnib and 2-APB Potentiates Anticancer Effects

Stromal interacting molecule (STIM1) is the $Ca^{2+}$ sensor in the ER and Orai1 is the plasmalemmal pore-forming subunit (Liou et al., 2005; Roos et al., 2005; Zhang et al., 2005; Feske et al., 2006; Mercer et al., 2006; Prakriya et al., 2006; Spassova et al., 2006; Vig et al., 2006; Yeromin et al., 2006; Zhang et al., 2006). The co-expression of STIM1 and Orai1 produces extremely large $I_{CRAC}$ currents which have the same biophysical and pharmacological properties as endogenous $I_{CRAC}$, including complete inhibition by low concentrations of $Gd^{3+}$ and bimodal sensitivity to 2-aminoethyldiphenyl borate (2-APB). Following these initial findings several other homologs of these proteins were identified including STIM2, Orai2, and Orai3. STIM2, like STIM1, has been shown to respond to decreases in ER $Ca^{2+}$ concentrations and to trigger activation of Orai1 (Brandman O, et al. (2007) STIM2 is a feedback regulator that stabilizes basal cytosolic and endoplasmic reticulum $Ca^{2+}$ levels. *Cell* 131:1327-1339). Similarly, both Orai2 and Orai3 have been shown to form functional channels that are activated upon ER depletion (DeHaven W I, Smyth J T, Boyles R R and Putney J W, Jr. (2007) Calcium inhibition and calcium potentiation of Orai1, Orai2, and Orai3 calcium release-activated calcium channels. *J Biol Chem* 282:17548-17556; Gross S A, et al. (2007) Murine ORAI2 splice variants form functional $Ca^{2+}$ release-activated $Ca^{2+}$ (CRAC) channels. *J Biol Chem* 282:19375-19384). Most of these studies involved exogenous expression of these proteins and less is known about the proteins' characteristics in native cells. For example, some reports suggest that Orai3 contribute little to endogenous $I_{CRAC}$, but these experiments have been confounded by the fact that siRNA knockdown of Orai3 results in enhanced expression of Orai1 mRNA. Thus, the lack of depression of store-operated $Ca^{2+}$ entry (SOCE) by Orai3 knockdown may be due to a compensatory upregulation of SOCE through Orai1-containing channels. It is also unknown if these subunits can co-assemble in native cells to form heteromeric channels.

The pharmacology of the channels also remains poorly understood and there are few ligands selective for these channels. Gadolinium continues to be the most selective inhibitor of Orai-containing channels. These channels also exhibit complex responses to 2-APB. Both endogenously and exogenously expressed Orai 1 channels are potentiated at concentrations of 2-APB below 5 µM but inhibited by higher concentrations, whereas Orai2 seems to have a transient potentiation at concentrations of 2-APB≦20 µM and also blocked by higher concentrations (DeHaven W I, et al. (2008) Complex actions of 2-aminoethyldiphenyl borate on store-operated calcium entry. *J Biol Chem* 283:19265-19273). In contrast, Orai3 channels are potentiated by 2-APB even at 50 µM and do not seem to be blocked by concentrations as high as 200 µM, indicating that Orai3 containing channels are likely involved in the effects of tipfarnib.

Figure 10:
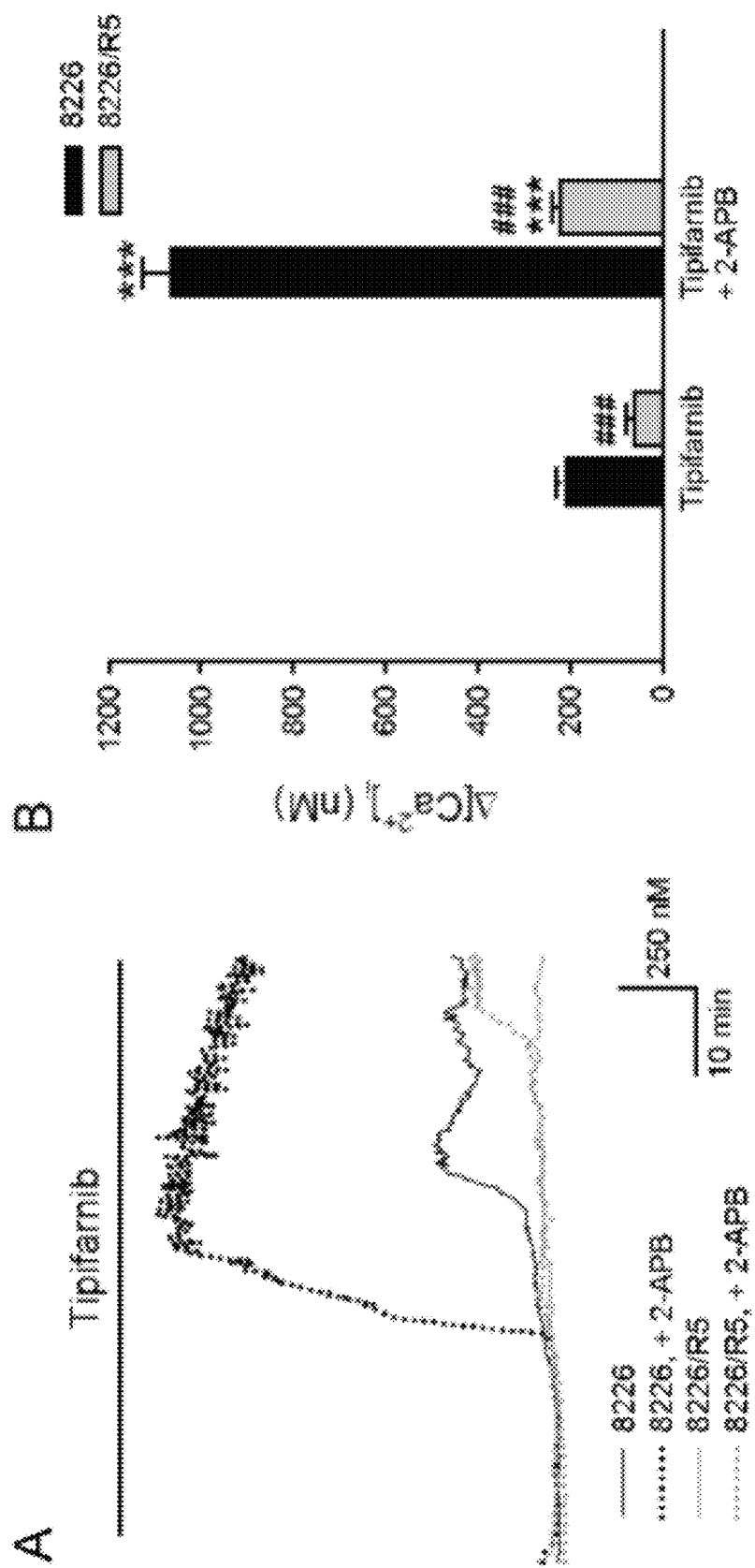
FIGS. 10(a)-(b) are graphs showing 2-APB potentiates tipifarnib-induced increases in $[Ca^{2+}]_i$ in both 8226 and 8226/R5 cells. (A) Representative traces of $[Ca^{2+}]_i$ recorded from four cells exposed to 5 µM tipifarnib in the absence and presence of 100 µM 2-APB (+2-APB). Bar across top of traces indicates duration of tipifarnib application. 2-APB was applied for 5 min prior to and during tipifarnib application. (B) Mean peak change in $[Ca^{2+}]_i$ observed in 8226 (n=63) and 8226/R5 (n=47) cells upon application of 5 µM tipifarnib alone or tipifarnib in combination with 100 µM 2-APB (8226, n=45; 8226/R5, n=82). Asterisks indicate significant difference from tipifarnib alone for each cell type (p<0.001) and pound symbols indicate significant difference between the cell types within each treatment (i.e. tipifarnib alone or tipifarnib+2-APB).
Figure 11:
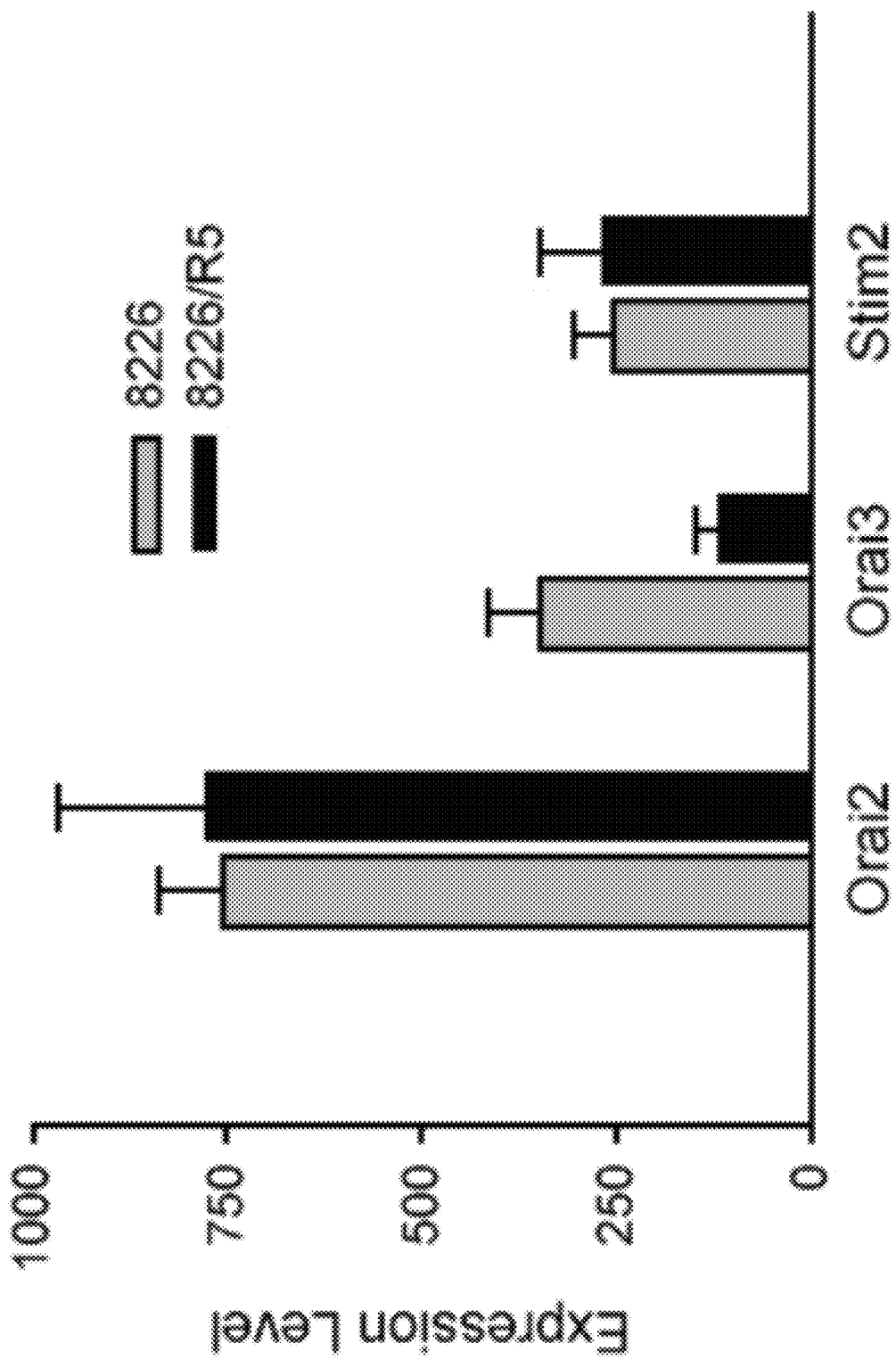
FIG. 11 is a graph showing tipifarnib-sensitive leukemia cell lines express higher levels of Orai3 than those which are tipifarnib-insensitive. Levels of Orai3, Orai2 and STIM2 gene expression determined using an Affymetrix U133A human gene array. Signal represents the expression value recorded with the gene chip normalized to β-actin expression.

The unexpected results obtained when co-administering tipifarnib and 2-APB in U937 cells was explored to determine whether 2-APB induces potentiation of tipifarnib in other hematopoietic tumor cells. FIG. 10(a) shows representative traces of $[Ca^{2+}]_i$ following tipifarnib application in 8226 and 8226/R5 cells in the absence and presence of 2-APB. As in U937 cells, 2-APB enhanced $[Ca^{2+}]_i$ increases in response to tipifarnib in both the 8226 and 8226/R5. These increases were statistically significant, as indicated in FIG. 10(b). Interestingly, 2-APB potentiated the $[Ca^{2+}]_i$ elevations in 8226/R5 to the extent that they were statistically indistinguishable from those of 8226 cells recorded in the absence of 2-APB. The elevations in $[Ca^{2+}]_i$ observed in 8226/R5 following co-application of 2-APB and tipifarnib did not exhibit the transient kinetics of those detected in the absence of 2-APB, seen in FIG. 10(a). Moreover, co-administration of 2-APB with tipifarnib potentiated tipifarnib and further reduced cellular growth, as seen in FIG. 11.

Experiments were carried out to determine if 2-APB could also influence the response to tipifarnib in 8226 and 8226/R5 cells. FIG. 4(a) shows traces of characteristic changes in $[Ca^{2+}]_i$ observed in 8226 and 8226/R5 cells when tipifarnib (5 µM) was applied alone or with 100 µM 2-APB. The tipifarnib-induced increase in $[Ca^{2+}]_i$ were potentiated by 2-APB in both cell lines. 2-APB amplified the tipifarnib-evoked increase in $[Ca^{2+}]_i$ by ~400% in 8226 cells, as seen in FIG. 4(b). In 8226/R5 cells the increase was ~250%, and this potentiation changed the amplitude of the response (226±12 nM) such that it was comparable to that seen in 8226 cells in the absence of 2-APB (215±17 nM), as seen in FIG. 4(b). FIG. 6(b) shows a bar graph of the relative growth rate of U937 cells as a function of tipifarnib concentration in the absence and presence of 2-APB at the indicated concentrations. Both low (5 µM) and high (100 µM) concentrations of 2-APB failed to prevent tipifarnib-evoked effects on cell survival, but conversely, enhanced cell death. Subsequent studies using HEK 293 cells overexpressing TRPM2 and TRPM7 indicated that tipifarnib does not directly affect those channels (data not shown). While the results obtained with 2-APB indicate that the conventional $I_{CRAC}$ consisting of Orai1 subunits are unlikely to produce these effects, they indicate that the Orai1 homolog, Orai3, is likely involved. Unlike both Orai1 and Orai2, Orai3 channels are not inhibited by 2-APB. Conversely, Orai3 channels heterologously overexpressed in HEK 293 cells are potentiated, and in some cases even directly activated, by application of 2-APB (DeHaven W I, et al. (2008) Complex actions of 2-aminoethyldiphenyl borate on store-operated calcium entry. *J Biol Chem* 283:19265-19273; Schindl R, et al. (2008) 2-aminoethoxydiphenyl borate alters selectivity of Orai3 channels by increasing their pore size. *J Biol Chem* 283:20261-20267).

While the results obtained with 2-APB indicate that the conventional $I_{CRAC}$ consisting of Orai1 subunits are unlikely to produce these effects, they raise the possibility that the Orai1 homolog, Orai3, may be involved. Unlike both Orai1 and Orai2, Orai3 channels are not inhibited by 2-APB (DeHaven W I, et al. Complex actions of 2-aminoethyldiphenyl borate on store-operated calcium entry. J Biol Chem2008 Jul. 11; 283(28):19265-73; Schindl R, et al. 2-aminoethoxydiphenyl borate alters selectivity of Orai3 channels by increasing their pore size. J Biol Chem2008 Jul. 18; 283(29): 20261-7). Conversely, Orai3 channels heterologously overexpressed in HEK 293 cells are potentiated, and in some cases even directly activated, by application of 2-APB (DeHaven W I, et al. Complex actions of 2-aminoethyldiphenyl borate on store-operated calcium entry. J Biol Chem2008 Jul. 11; 283 (28):19265-73; Schindl R, et al. 2-aminoethoxydiphenyl borate alters selectivity of Orai3 channels by increasing their pore size. J Biol Chem2008 Jul. 18; 283(29):20261-7). This motivated us to retrospectively analyze gene array data previously collected by Drs. Darrin Beaupre and Lori Hazlehurst. Table 1 summarizes the results obtained and shows a trend of Orai3 being expressed at lower levels in cells resistant to tipifarnib. No such trend was observed for the genes of other known $I_{CRAC}$ constituents, Orai2 or the STIM2.

To confirm the function of Orai3, $[Ca^{2+}]_i$ levels were analyzed using the conventional method for monitoring SOCE, seen in FIGS. 9(a)-(c). Intracellular $Ca^{2+}$ stores were depleted by preincubating the cells in thapsigargin (8 µM, 30 min, 37° C.) in a $Ca^{2+}$-free saline solution. Such depletion of store $Ca^{2+}$ in the absence of extracellular $Ca^{2+}$ results in activation of Orai-containing store-operated $Ca^{2+}$ channels while eliminating $Ca^{2+}$-dependent inactivation. Following washout of thapsigargin, cells were once again bathed in a $Ca^{2+}$-free solution followed by application of saline solution containing 2.5 mM $Ca^{2+}$. The $Ca^{2+}$ influx observed under these conditions is SOCE and indicative of Orai activity. Upon $Ca^{2+}$ "add-back", elevations in $[Ca^{2+}]_i$ were observed in all cell lines tested, seen in FIGS. 9(a) and (b). However, the elevations in $[Ca^{2+}]_i$ observed in the tipifarnib-sensitive 8226 cells were greater than those observed in the tipifarnib-resistant 8226/R5 cells. This difference in add-back induced increases in $[Ca^{2+}]_i$ was statistically significant, as seen in FIG. 9(c). The $[Ca^{2+}]_i$ responses to $Ca^{2+}$ add-back recorded from U937 cells were similar to those observed in 8226 cells, but those recorded from the multiple myeloma cell line, H929, were statistically greater than those of all other cell lines, as seen in FIG. 9(c). Unlike the responses observed to tipifarnib, the elevations in $[Ca^{2+}]_i$ elicited under these conditions were transient and did not result in disruption of the plasma membrane. Orai channels exhibit $Ca^{2+}$-dependent inactivation, which likely accounts for the observed phenomenon. Thus, tipifarnib must not only activate the channel, but must also prevent inactivation of SOC.

Figure 12:
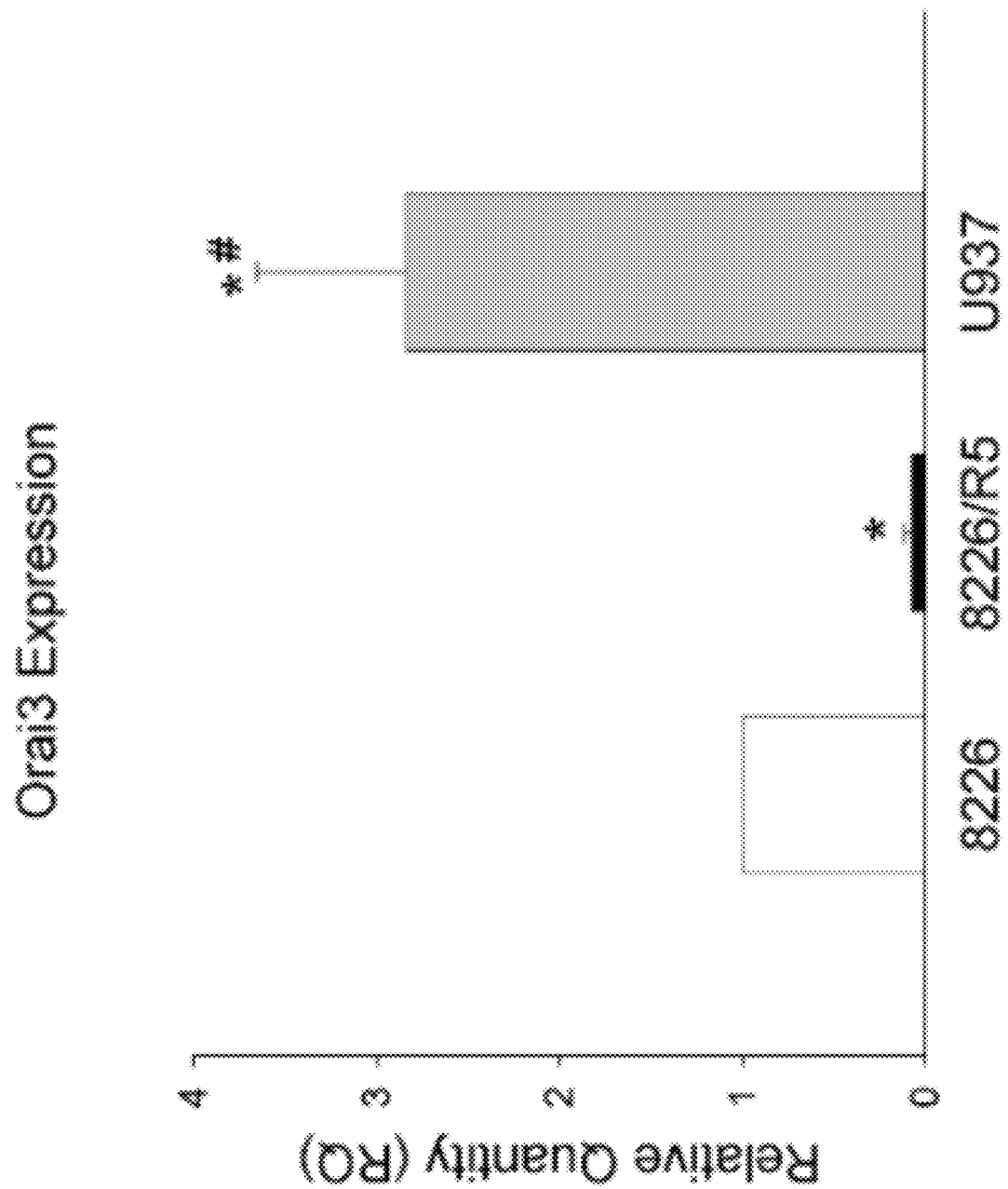
FIG. 12 is a graph showing higher expression of Orai3 mRNA in tipifarnib-sensitive leukemia cell lines. Mean relative quantity (RQ) (±SEM) of Orai3 transcripts detected in mRNA extracts from U937, 8226 and 8226/R5 cells. Asterisk indicates significant difference from 8226 cells and pound symbol denotes significant difference in Orai3 expression between U937 and 8226/R5 cells (n=3 and p<0.05 for all).
Figure 13:
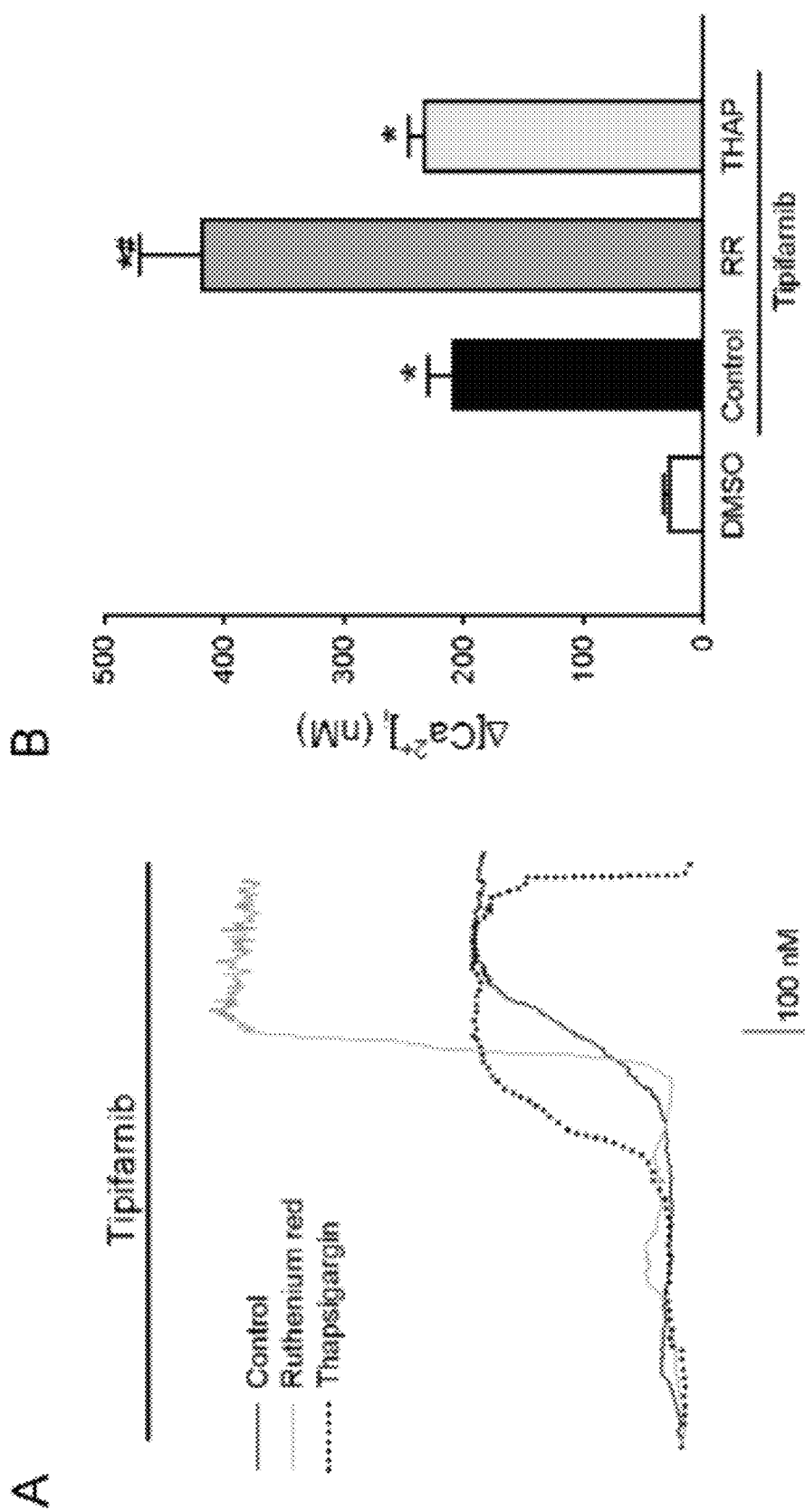
FIGS. 13(a)-(b) are graphs showing tipifarnib-induced elevations in $[Ca^{2+}]_i$ are not due to mobilization of $Ca^{2+}$ from intracellular stores. (A) Characteristic increases in $[Ca^{2+}]_i$ elicited from three U937 cells by application of tipifarnib (5 µM) alone (Control) or in the presence of 100 nM ruthenium red, or when tipifarnib was applied after preincubation of the cells in 10 µM thapsigargin (Thapsigargin). (B) Mean peak increases in $[Ca^{2+}]_i$ observed in response to bath application of vehicle (DMSO) (n=42), 5 µM tipifarnib (Control, n=17), 5 µM tipifarnib in the presence of 100 nM ruthenium red (RR, n=56), or 5 µM tipifarnib following preincubation in 10 µM thapsigargin (THAP, n=19). Asterisk denotes significant difference from vehicle control (DMSO) (p<0.01) and pound symbol denotes significant difference from Control group (p<0.01).

Analysis of a gene array data, seen in FIG. 11 and Table 1, summarizes the results obtained and shows a trend of Orai3 being expressed at lower levels in cells resistant to tipifarnib. No such trend was observed for the Orai2 or the STIM2 gene. While no statistical significance was observed when a t-test was performed (p<0.06) comparing 8226 cell types that were sensitive to tipifarnib (8226/S and 8226/LR5) with the insensitive daughter line (8226/R5), the power of this test (0.445) was below the desired power (0.8). Quantitative RT-PCR experiments were used to precisely measure the expression levels of Orai and STIM subunits in U937, 8226, 8226/R5, and H929 cells. FIG. 12 shows a bar graph of mean relative quantity (RQ) obtained for 3 experiments testing for Orai3 expression. Consistent with the gene array date, the levels of Orai3 measured in both U937 and 8226 cells were significantly greater than those measured in the tipifarnib-insensitive 8226/R5 cells.

TABLE 1

Tipifarnib-sensitive leukemia cell lines express higher levels of Orai3 than those which are tipifarnib-insensitive

| Cell Type | Orai3 | | Tipifarnib sensitivity |
|---|---|---|---|
| | Signal | Detection | |
| U937 | 959.5 | P | Yes |
| 8226 S | 365.5 | P | Yes |
| 8226 S | 290.2 | P | Yes |
| 8226 LR5 | 550.7 | P | Yes |
| 8226 LR5 | 356.9 | P | Yes |
| 8226 R5 | 186.6 | P | No |
| 8226 R5 | 156.7 | P | No |

Levels of Orai3 gene expression determined using an Affymetrix U133A human gene array. Signal represents the raw expression value recorded with the gene chip and the Detection indicates if the raw expression signal is noise (A, absent) or considered to show expression (P, present).

Reintroduction of $Ca^{2+}$ following store depletion ($Ca^{2+}$ add-back protocol) provided insight into the role of SOC in $Ca^{2+}$ handling in multiple myeloma cells. As was noted above, Orai channels exhibit $Ca^{2+}$-dependent inactivation. Correlating ER $Ca^{2+}$ loading with SOC activity, or the $[Ca^{2+}]_i$ increases observed upon reintroduction of extracellular $Ca^{2+}$, are seen in FIG. 10(a).

Example 5

Discussion

Specific subgroups of AML patients benefit from tipifarnib treatment (Raponi M, et al. (2007) Identification of molecular predictors of response in a study of tipifarnib treatment in relapsed and refractory acute myelogenous leukemia. *Clin Cancer Res* 13:2254-2260; Raponi M, et al. (2008) A 2-gene classifier for predicting response to the farnesyltransferase inhibitor tipifarnib in acute myeloid leukemia. Blood 111: 2589-2596). Two genes were identified as being predictors of response and one of these genes, RASGRP1 is linked to Ras signaling. However, the molecular mechanism by which tipifarnib triggers cell death still remains elusive, and has not been unequivocally associated with farnesyltransferase inhibition. Interestingly, it was recent noted that modifications made to the core structure of tipifarnib, generating novel bezofuran FTIs, showed that the antiproliferative properties of the tipifarnib analogs were not directly related to their affinity for farnesyltransferase (Asoh K, et al. (2009) Synthesis and structure-activity relationships of novel benzofuran farnesyltransferase inhibitors. *Bioorg Med Chem Lett* 19:1753-1757). Some tipifarnib analogs with high FTI activity failed to inhibit QG56 tumor cell growth, suggesting that FTI activity alone in not antiproliferative in this model, seen above.

Several studies have linked apoptosis to calcium signaling pathways as a response to cellular stress (Orrenius S, et al. Regulation of cell death: the calcium-apoptosis link Nat Rev Mol Cell Biol. 2003 July; 4(7):552-65). ER stress induces apoptosis via two different mechanisms, the unfolded protein response and dysregulation of $Ca^{2+}$ homeostasis (Ferri K F, Kroemer G. Organelle-specific initiation of cell death pathways. Nat Cell Biol. 2001 November; 3(11):E255-63; Lee K, et al. IRE1-mediated unconventional mRNA splicing and S2P-mediated ATF6 cleavage merge to regulate XBP1 in signaling the unfolded protein response. Genes Dev. 2002 Feb. 15; 16(4):452-66). The data shows that agents which inhibit or potentiate tipifarnib-induced $[Ca^{2+}]_i$ overload diminish or enhance the apoptosis promoted by this drug, respectively, and indicates that this increase in $[Ca^{2+}]_i$ is directly linked to the influence of tipifarnib on cell survival. For example, several plasma membrane calcium channels have been identified in U937 cells that likely account for the elevations in intracellular calcium and concomitant cell death in response to tipifarnib application.

These channels include store-operated calcium channels, TRPM2 and TRPM7 (Lee Y K, et al. Characterization of $Ca^{2+}$ influx induced by dimethylphytosphingosine and lysophosphatidylcholine in U937 monocytes. Biochem Biophys Res Commun 2006 Sep. 29; 348(3):1116-22; Willmott N J, et al. Functional importance of the dihydropyridine-sensitive, yet voltage-insensitive store-operated $Ca^{2+}$ influx of U937 cells. FEBS Lett. 1996 Sep. 30; 394(2):159-64; Zhang W, et al. TRPM2 is an ion channel that modulates hematopoietic cell death through activation of caspases and PARP cleavage. Am J Physiol Cell Physiol. 2006 April; 290(4):C1146-59). Unlike SOC, TRPM2 has been shown to be pro-apoptotic in multiple cell types. TRPM2 is activated by $H_2O_2$ and tissue necrosis factor α (TNF-α) and has been suggested to evoke cell death in response to oxidative stress. TRPM2 is activated by $H_2O_2$ and tissue necrosis factor α (TNF-α) and has been suggested to evoke cell death in response to oxidative stress. In U937 cells, activation of TRPM2 with either $H_2O_2$ or TNF-α increased cleavage of caspase-8, -9, -3 and -7 and PARP, and consequently, cell death was enhanced (Zhang W, et al. TRPM2 is an ion channel that modulates hematopoietic cell death through activation of caspases and PARP cleavage. Am J Physiol Cell Physiol 2006 April; 290(4):C1146-59). The caspase/PARP cleavage and death of the U937 cells was directly linked to the intracellular $Ca^{2+}$ elevations mediated by TRPM2 activation. However, TRPM2 channels are not inhibited by concentrations of $La^{3+} \leq 100$ μM (Kraft R, et al. Hydrogen peroxide and ADP-ribose induce TRPM2-mediated calcium influx and cation currents in microglia. Am J Physiol Cell Physiol 2004 January; 286(1):C129-37), and low concentrations of this trivalent cation blocked both the $Ca^{2+}$ increases and cell death evoked by tipifarnib. Furthermore, TRPM2 channels heterologously expressed in HEK-293 cells are blocked by 2-APB with an $IC_{50}$ of 1 μM, but a second study, also on TRPM2 expressed in the same HEK-293 cells showed that the channels are not blocked by 2-APB even at a concentration of 150 μM (Xu S Z, et al. Block of TRPCS channels by 2-aminoethoxydiphenyl borate: a differential, extracellular and voltage-dependent effect. Br J Pharmacol 2005 June; 145(4):405-14). The reason for this discrepancy is not clear, but it does appear that the pharmacological properties of the tipifarnib-activated conductance are not consistent with TRPM2.

Like TRPM2, TRPM7 is activated by $H_2O_2$ and is believed to be involved in oxidative stress-induced cell death. Overexpression of TRPM7 in HEK-293 cells results in cell swelling, detachment and death (Nadler M J, et al. LTRPC7 is a Mg.ATP-regulated divalent cation channel required for cell viability. Nature. 2001 May 31; 411(6837):590-5). However, 10 μM $La^{3+}$ and $Gd^{3+}$ failed to inhibit TRPM7 channels heterologously expressed in HEK-293 cells (Monteilh-Zoller M K, et al. TRPM7 provides an ion channel mechanism for cellular entry of trace metal ions. J Gen Physiol. 2003 January; 121(1):49-60), and 1 mM concentrations of these ions was required to inhibit TRPM7. Thus, the tipifarnib-activated $Ca^{2+}$ conductance does not share these properties with TRPM7, since 200 nM $La^+$ was sufficient to abolish both the $Ca^{2+}$ elevations and the cell death evoked by the FTI and 100 μM $Gd^{3+}$ produced a near complete block of the $Ca^{2+}$ increase. Also, 100 μM 2-APB blocks ~25% of TRPM7-evoked currents (Li M, et al. Functional characterization of homo- and heteromeric channel kinases TRPM6 and TRPM7. J Gen Physiol. 2006 May; 127(5):525-37), but has no effect on either $Ca^+$ elevations or U937 cell death evoked by tipifarnib. While activation of TRPM7 has been associated with cell death, inhibition of the channel can also affect cell survival. The targeted deletion of TRPM7 in the avian B-lymphocytes cell line, DT-40 B, is lethal (Nadler M J, et al. LTRPC7 is a Mg. ATP-regulated divalent cation channel required for cell viability. Nature. 2001 May 31; 411(6837): 590-5), and thus, inhibition of TRPM7 by 2-APB may contribute to the enhanced cell death observed when tipifarnib and 2-ABP were co-applied.

Figure 14:
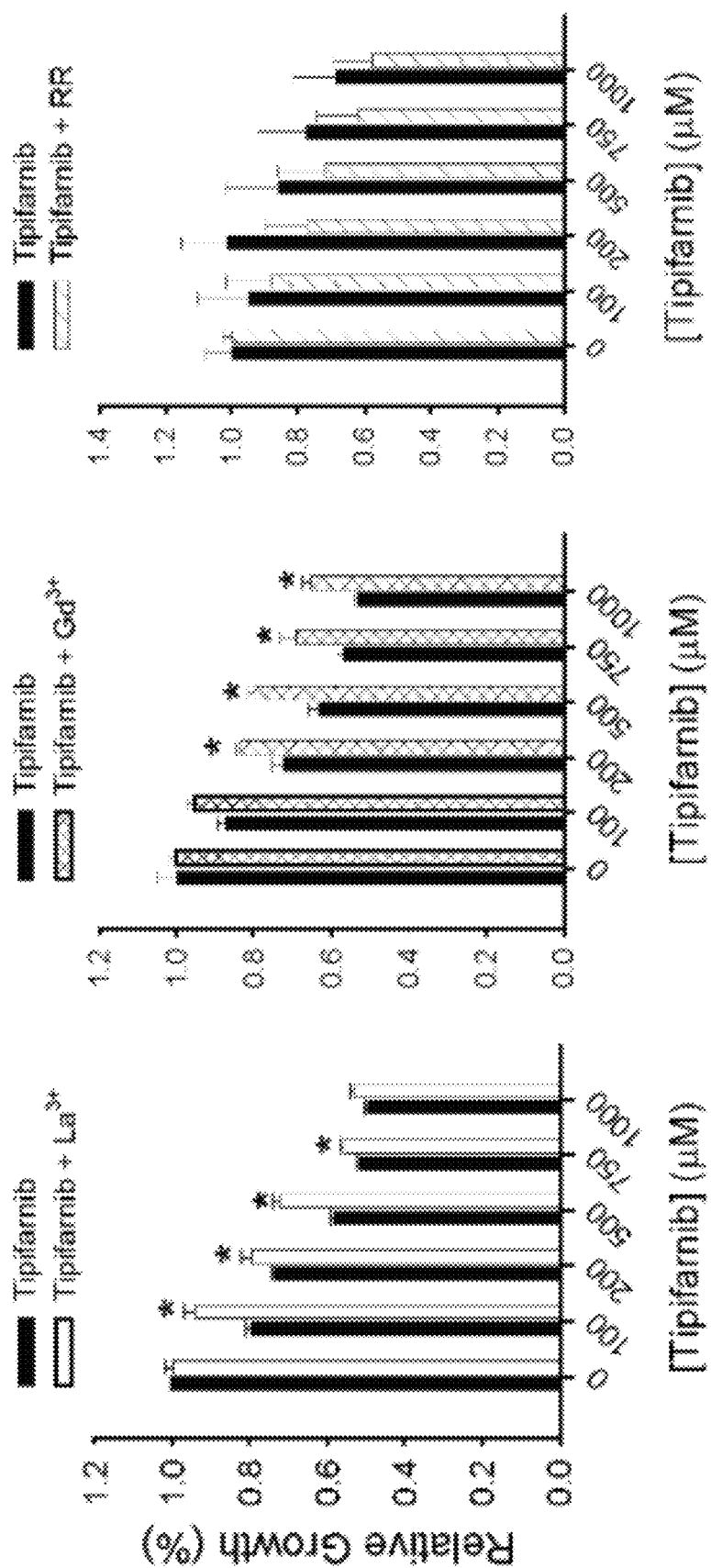
FIG. 14(a)-(c) are graphs showing inhibition of tipifarnib-induced $Ca^{2+}$ influx by (A) $La^{3+}$, (B) $Gd^{3+}$, and (C) ruthenium red.

To date, there is little evidence linking the activation of store-operated calcium channels and cell death. A recent study on cervical epithelial cells indicates that soft substrate-induced apoptosis is mediated by the interaction of the calcium sensor, stromal interacting molecule 1 (STIM1), and the pore-forming subunit (Orai1) of store-operated calcium channels (Chiu W T, et al. Soft substrate up-regulates the interaction of STIM1 with store-operated $Ca^{2+}$ channels that lead to normal epithelial cell apoptosis. Mol Biol Cell 2008 May; 19(5):2220-30). Upon contact with soft substrate, SOC activity is upregulated and $Ca^{2+}$ homeostasis disturbed in normal cervical epithelial cells, which in turn triggers a pro-apoptotic signaling cascade involving μ-calpain (Chiu W T, et al. Soft substrate up-regulates the interaction of STIM1 with store-operated $Ca^{2+}$ channels that lead to normal epithelial cell apoptosis. Mol Biol Cell 2008 May; 19(5):2220-30). Interestingly, the activation of SOC is depressed in malignant cervical epithelial cells, and these cells do not undergo soft-substrate-induced apoptosis (Chiu W T, et al. Soft substrate up-regulates the interaction of STIM1 with store-operated $Ca^{2+}$ channels that lead to normal epithelial cell apoptosis. Mol Biol Cell 2008 May; 19(5):2220-30). The inhibition of tipifarnib-induced $Ca^{2+}$ influx and lack of tipifarnib-mediated growth inhibition by $La^{3+}$ and $Gd^{3+}$ is consistent with an Orai1-containing SOC-mediated phenomenon, as seen in FIGS. 14(a)-(c). However, Orai1-containing SOC are inhibited by 100 μM 2-APB, and thus the activation the potentiation of tipifarnib effects by this drug is inconsistent with an Orai1-mediated effect. Unlike Orai1-containing channels, the related SOC subunit, Orai3 has been shown to form functional SOC that are potentiated by 2-APB (DeHaven W I, et al. Complex actions of 2-aminoethyldiphenyl borate on store-operated calcium entry. J Biol Chem2008 Jul. 11; 283(28): 19265-73; Schindl R, et al. 2-aminoethoxydiphenyl borate alters selectivity of Orai3 channels by increasing their pore size. J Biol Chem2008 Jul. 18; 283(29):20261-7). Gene array data and qRT-PCR experiments confirm that Orai3 is expressed in both U937 and 8226 cells. Importantly, the 8226/R5 daughter cell line which is resistant to tipifarnib expresses Orai3 at significantly lower levels than the tipifarnib-sensitive 8226 parent line. Co-application of 2-APB with tipifarnib potentiates the effects of tipifarnib on the resistant 8226/R5 cells, indicating that tipifarnib sensitivity may be conferred in this manner.

Tipifarnib activates a plasma membrane channel in U937 cells which produces pronounced elevations in $[Ca^{2+}]_i$ that consequently evoke apoptosis in these cells. The increases in $[Ca^{2+}]_i$ evoked by tipifarnib result in ER stress, and the drug-induced cell death may be diminished or enhanced by blocking or potentiating these changes in $[Ca^{2+}]_i$, respectively. Further, the data demonstrates that induction of ER stress can overcome cell adhesion-mediated drug resistance, and thus, de novo drug resistance.

Both tipifarnib and bortezomib as single agents and in combination overcome cell adhesion mediated drug resistance (CAM-DR) and induce ER-stress in multiple myeloma and acute myeloid leukemic cells. The findings presented here show a unique pathway specifically induced by tipifarnib, but not by other FTIs, that causes intracellular free $Ca^{2+}$ elevations to induce ER stress mediated cell death.

Resistance to chemotherapeutic agents continues to be a major impediment in the successful treatment of hematopoietic cancers. The contribution of the tumor microenvironment to the resistance phenotype has been extensively investigated. Most specifically the adhesion of hematopoietic cells to fibronectin or bone marrow stromal cells causes resistance to a broad spectrum of cytotoxic agents (Hazlehurst L A, et al. Reduction in drug-induced DNA double-strand breaks associated with beta1 integrin-mediated adhesion correlates with drug resistance in U937 cells. Blood. 2001 Sep. 15; 98(6): 1897-903). Thus, the identification of any compounds that are capable of overcoming resistance would prove to be valuable. Notably this report demonstrates that adhesion to fibronectin does not protect tumor cells from ER-stress induced apoptosis when either classical ER stressors such as thapsigargin are used or when tipifarnib is used to trigger this pathway.

In the preceding specification, all documents, acts, or information disclosed do not constitute an admission that the document, act, or information of any combination thereof was publicly available, known to the public, part of the general knowledge in the art, or was known to be relevant to solve any problem at the time of priority.

The disclosures of all publications cited above are expressly incorporated herein by reference, each in its entirety, to the same extent as if each were incorporated by reference individually.

While there has been described and illustrated specific embodiments of a composition and method for treatment of myeloid cancer, it will be apparent to those skilled in the art that variations and modifications are possible without deviating from the broad spirit and principle of the present invention. It is also to be understood that the following claims are intended to cover all of the generic and specific features of the invention herein described, and all statements of the scope of the invention which, as a matter of language, might be said to fall therebetween.

What is claimed is:

1. A composition comprising:
   between 100 nM and 10,000 nM of tipifarnib; and
   between 1 μM and 200 μM of 2-aminoethoxydiphenyl borate.

2. A composition comprising between 100 mg and 1,200 mg of tipifarnib and between 1 mg/kg and 3 mg/kg of 2-aminoethoxydiphenyl borate.

3. The composition of claim 2, wherein the tipifarnib is between 400 mg and 1,200 mg.

4. The composition of claim 3, wherein the tipifarnib is at 600 mg.

5. The composition of claim 1, further comprising bortezomib.

6. The composition of claim 2, further comprising bortezomib.

7. The composition of claim 6, wherein the bortezomib is administered between 0.7 mg/m$^2$ and 1.3 mg/m$^2$.

* * * * *